United States Patent
Dan et al.

(10) Patent No.: US 10,531,943 B1
(45) Date of Patent: *Jan. 14, 2020

(54) SYSTEMS AND METHODS FOR IMPLANT DELIVERY

(71) Applicant: JAVELIN MEDICAL LTD., Yokneam (IL)

(72) Inventors: Yair Dan, Moshav Kefar Kisch (IL); Avraham Neta, Gilon (IL); Guy Shinar, Ramat Gan (IL); Ofer Yodfat, Modi'In (IL)

(73) Assignee: JAVELIN MEDICAL LTD., Yokneam (IL)

( * ) Notice: Subject to any disclaimer, the term of this patent is extended or adjusted under 35 U.S.C. 154(b) by 314 days.

This patent is subject to a terminal disclaimer.

(21) Appl. No.: 15/452,086

(22) Filed: Mar. 7, 2017

Related U.S. Application Data

(63) Continuation of application No. 14/563,513, filed on Dec. 8, 2014, now Pat. No. 9,592,110.

(Continued)

(51) Int. Cl.
*A61F 2/01* (2006.01)
*A61B 17/34* (2006.01)

(52) U.S. Cl.
CPC .......... *A61F 2/013* (2013.01); *A61B 17/3403* (2013.01); *A61B 2017/3413* (2013.01);
(Continued)

(58) Field of Classification Search
CPC A61F 2/01; A61F 2002/011; A61F 2002/016; A61F 2230/0091;
(Continued)

(56) References Cited

U.S. PATENT DOCUMENTS

| 3,540,431 A | 11/1970 | Mobin-Uddin |
| 4,425,908 A | 1/1984 | Simon |

(Continued)

FOREIGN PATENT DOCUMENTS

| CN | 2601642 | 2/2004 |
| CN | 1911188 A | 2/2007 |

(Continued)

OTHER PUBLICATIONS

Cogo et al. "Distribution of Thrombosis in Patients with Symptomatic Deep Vein Thrombosis" Arch Intern Med., 1993, vol. 153, p. 2777-2780.

(Continued)

*Primary Examiner* — Katherine M Shi
(74) *Attorney, Agent, or Firm* — Cooley LLP

(57) ABSTRACT

Some embodiments of the present disclosure are directed generally to systems and methods for delivering an implant to a body vessel of a patient. Such disclosed implants may be a monofilament implant, and disclosed systems for implanting the implant may be automatic. Some embodiments may enable retraction of said implant back into the delivery system following partial exteriorization of the implant from the delivery system. Some embodiments may be configured for retraction of said implant from the patient's body following complete exteriorization of the implant from the delivery system. Some of the embodiments are directed at delivering a monofilament implant for preventing embolic stroke. Other embodiments are directed at preventing pulmonary embolism, occluding a body vessel such as the left atrial appendage, occluding a body passageway such as a patent foramen ovalae, stenting a body vessel, or releasing a local therapeutic agent such as a drug or ionizing radiation.

19 Claims, 13 Drawing Sheets

Related U.S. Application Data

(60) Provisional application No. 61/912,655, filed on Dec. 6, 2013.

(52) U.S. Cl.
CPC ... *A61F 2002/011* (2013.01); *A61F 2002/016* (2013.01); *A61F 2220/005* (2013.01); *A61F 2220/0008* (2013.01); *A61F 2220/0058* (2013.01); *A61F 2230/0091* (2013.01)

(58) Field of Classification Search
CPC ............... A61F 2230/0071; A61F 2/88; A61B 17/12109; A61B 17/12031; A61B 17/12036; A61B 17/0057; A61B 2017/00867
USPC .................................................. 606/151, 200
See application file for complete search history.

(56) References Cited

U.S. PATENT DOCUMENTS

| | | |
|---|---|---|
| 4,494,531 A | 1/1985 | Gianturco |
| 4,722,350 A | 2/1988 | Armeniades et al. |
| 5,059,205 A | 10/1991 | El-Nounou et al. |
| 5,350,397 A | 9/1994 | Palermo et al. |
| 5,413,586 A | 5/1995 | Dibie et al. |
| 5,634,942 A | 6/1997 | Chevillon et al. |
| 5,800,454 A | 9/1998 | Jacobsen et al. |
| 5,957,940 A | 9/1999 | Tanner et al. |
| 5,976,172 A | 11/1999 | Homsma et al. |
| 6,007,558 A | 12/1999 | Ravenscroft et al. |
| 6,059,825 A | 5/2000 | Hobbs et al. |
| 6,099,549 A | 8/2000 | Bosma et al. |
| 6,152,144 A | 11/2000 | Lesh et al. |
| 6,214,025 B1 | 4/2001 | Thistle et al. |
| 6,344,052 B1 | 2/2002 | Greenan et al. |
| 6,368,346 B1 | 4/2002 | Jadhav et al. |
| 6,375,671 B1 | 4/2002 | Kobayashi et al. |
| 6,395,017 B1 | 5/2002 | Dwyer et al. |
| 6,652,558 B2 | 11/2003 | Patel et al. |
| 6,673,089 B1 | 1/2004 | Yassour et al. |
| 6,730,108 B2 | 5/2004 | Van Tassel et al. |
| 7,128,073 B1 | 10/2006 | Van der Burg et al. |
| 7,144,363 B2 | 12/2006 | Pai et al. |
| 7,261,731 B2 | 8/2007 | Patel et al. |
| 7,306,624 B2 | 12/2007 | Yodfat et al. |
| 7,572,273 B2 | 8/2009 | Mazzocchi et al. |
| 7,704,267 B2 | 4/2010 | Tessmer |
| 7,716,801 B2 | 5/2010 | Douk et al. |
| 7,794,494 B2 | 9/2010 | Sahatjian |
| 8,057,507 B2 | 11/2011 | Horan et al. |
| 8,118,858 B2 | 2/2012 | Tseng et al. |
| 8,137,396 B2 | 3/2012 | Busold et al. |
| 8,206,412 B2 | 6/2012 | Galdonik et al. |
| 8,221,446 B2 | 7/2012 | Pal et al. |
| 8,236,009 B2 | 8/2012 | Saadat et al. |
| 9,220,588 B2 | 12/2015 | Shinar et al. |
| 9,592,110 B1 | 3/2017 | Dan et al. |
| 10,028,819 B2 | 7/2018 | Shinar et al. |
| 10,226,321 B2 | 3/2019 | Shinar et al. |
| 2001/0007946 A1 | 7/2001 | Lenker et al. |
| 2002/0010481 A1 | 1/2002 | Jayaraman |
| 2002/0188170 A1 | 12/2002 | Santamore et al. |
| 2003/0100939 A1 | 5/2003 | Yodfat et al. |
| 2004/0082962 A1 | 4/2004 | Demarais et al. |
| 2005/0004575 A1* | 1/2005 | Sgro ................... A61B 17/064 606/220 |
| 2006/0167489 A1 | 7/2006 | Satake et al. |
| 2006/0212047 A1 | 9/2006 | Abbott et al. |
| 2007/0010857 A1 | 1/2007 | Sugimoto et al. |
| 2007/0066863 A1 | 3/2007 | Rafiee et al. |
| 2007/0156123 A1 | 7/2007 | Moll et al. |
| 2008/0108933 A1 | 5/2008 | Yu et al. |
| 2008/0147111 A1 | 6/2008 | Johnson et al. |
| 2008/0183206 A1 | 7/2008 | Batiste |
| 2008/0221600 A1 | 9/2008 | Dieck et al. |
| 2008/0269789 A1 | 10/2008 | Eli |
| 2009/0054905 A1 | 2/2009 | Levy |
| 2009/0099591 A1 | 4/2009 | Nardone et al. |
| 2009/0138066 A1 | 5/2009 | Leopold et al. |
| 2009/0228020 A1 | 9/2009 | Wallace et al. |
| 2010/0016881 A1 | 1/2010 | Fleck et al. |
| 2010/0234852 A1 | 9/2010 | Shinohara et al. |
| 2010/0268204 A1 | 10/2010 | Tieu et al. |
| 2010/0280522 A1 | 11/2010 | Barry et al. |
| 2011/0021984 A1 | 1/2011 | Kirschenman et al. |
| 2011/0022149 A1 | 1/2011 | Cox et al. |
| 2011/0137394 A1 | 6/2011 | Lunsford et al. |
| 2011/0226379 A2 | 9/2011 | Johnson |
| 2012/0165919 A1 | 6/2012 | Cox et al. |
| 2012/0172921 A1 | 7/2012 | Yamanaka et al. |
| 2012/0197379 A1 | 8/2012 | Laske et al. |
| 2012/0245614 A1 | 9/2012 | Drasler |
| 2012/0289988 A1 | 11/2012 | Riina et al. |
| 2012/0316597 A1 | 12/2012 | Fitz et al. |
| 2013/0184658 A1 | 7/2013 | Duncan |
| 2014/0004503 A1 | 1/2014 | Cima et al. |
| 2014/0114337 A1 | 4/2014 | Fung et al. |
| 2014/0135799 A1 | 5/2014 | Henderson |
| 2014/0277097 A1 | 9/2014 | Castleberry et al. |
| 2015/0297241 A1 | 10/2015 | Yodfat et al. |
| 2017/0367808 A1 | 12/2017 | Shinar et al. |
| 2018/0103960 A1 | 4/2018 | Poulsen |
| 2019/0021836 A1 | 1/2019 | Yair et al. |
| 2019/0167404 A1 | 6/2019 | Shinar et al. |

FOREIGN PATENT DOCUMENTS

| | | | |
|---|---|---|---|
| CN | 2017/68049 U | 3/2011 | |
| CN | 103313751 A | 9/2013 | |
| EP | 0121447 | 10/1984 | |
| WO | WO 91/04716 | 4/1991 | |
| WO | WO 1998/034546 | 8/1998 | |
| WO | WO 2004/098420 | 11/2004 | |
| WO | WO 2005/051235 | 6/2005 | |
| WO | WO 2006/055443 | 5/2006 | |
| WO | WO 2006/084156 | 8/2006 | |
| WO | WO 2008/042266 | 4/2008 | |
| WO | WO 2011/014703 | 2/2011 | |
| WO | WO 2012/094251 | 7/2012 | |
| WO | WO 2013/179137 | 12/2013 | |
| WO | WO-2013179137 A2 * | 12/2013 | ......... A61B 17/0487 |
| WO | WO 2014/102767 | 7/2014 | |
| WO | WO 2014/111911 | 7/2014 | |

OTHER PUBLICATIONS

Cousin et al. "Incidence et distribution des thromboses veineusesdes des membres inférieurs diagnostiquées par écho-doppler au décours de prothèses de hanche, de genou et de fractures de hanche. Résultats portant sur 5981 explorations et 2123 thromboses en dix ans" Journal des Maladies Vasculaires, 2011, vol. 36, No. 4, p. 243-253 (English summary).

Decousus et al. "A Clinical Trial of Vena Caval Filters in the Prevention of Pulmonary Embolism in Patients with Proximal Deep-Vein Thrombosis", The New England Journal of Medicine, 1998, vol. 338, No. 7, p. 409-415.

Ouriel et al. "The anatomy of deep venous thrombosis of the lower extremity", Journal of Vascular Surgery, 2000, vol. 31, p. 895-900.

Thors et al. "Resorbable Inferior Vena Cava Filters: Trial in an In-vivo Porcine Model" J Vasc Interv Radiol 2011, vol. 22, No. 3, Mar. 2011, 330-335.

International Search Report and Written Opinion for International Application No. PCT/IB2013/001336 dated Jan. 24, 2014.

International Search Report for International Application No. PCT/IL13/50979 dated Jun. 23, 2014.

International Search Report for International Application No. PCT/IL13/50981 dated Jun. 23, 2014.

Supplementary European Search Report and European Search Opinion, dated Jan. 12, 2016, for European Application No. 13797107.3.

(56) References Cited

OTHER PUBLICATIONS

Supplementary European Search Report for European Application No. 13871655.0 dated Oct. 13, 2016.
International Search Report for International Application No. PCT/IL2016/050016 dated Jun. 9, 2016.
International Search Report for International Application No. PCT/IL2017/051157 dated May 7, 2018.

* cited by examiner

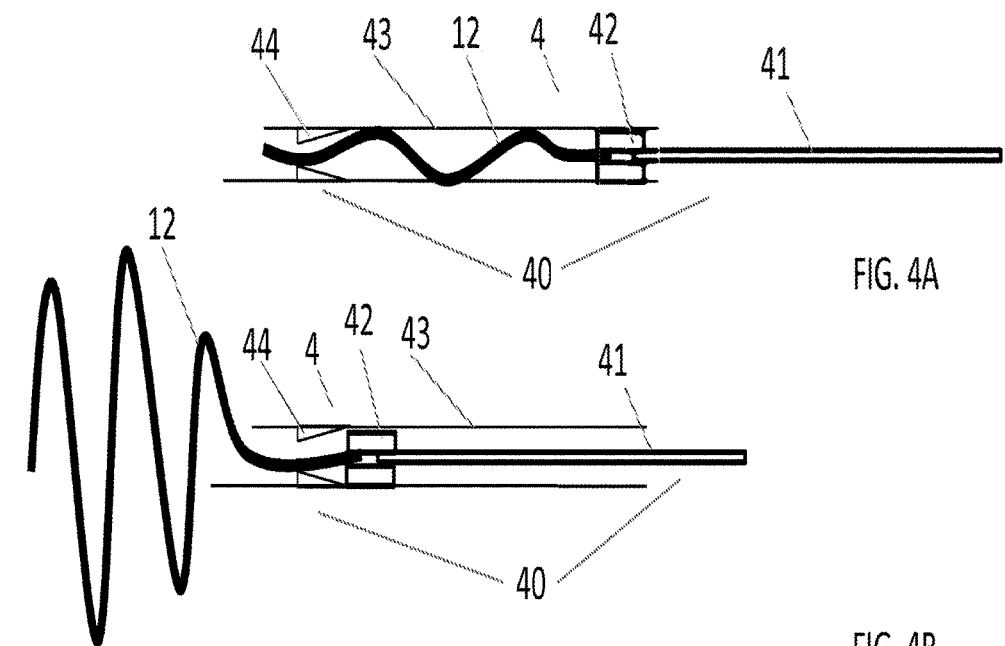
FIG. 4A
FIG. 4B
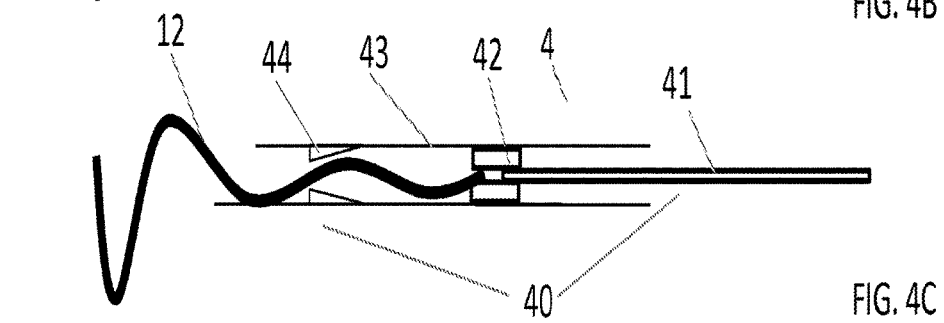
FIG. 4C
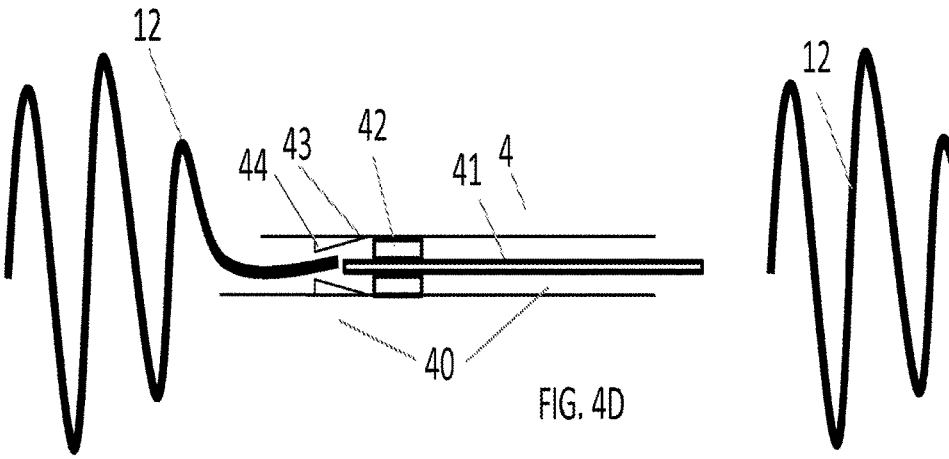
FIG. 4D
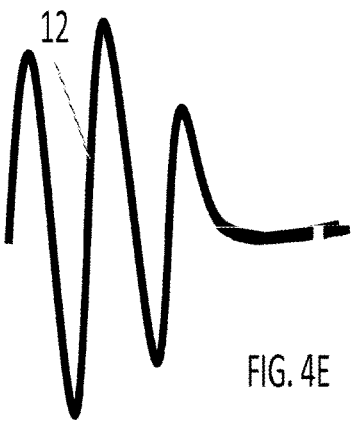
FIG. 4E

SYSTEMS AND METHODS FOR IMPLANT DELIVERY

RELATED APPLICATIONS

This application is a continuation of U.S. patent application Ser. No. 14/563,513, filed Dec. 8, 2014 (now U.S. Pat. No. 9,592,110), entitled "Systems and Methods for Implant Delivery," and claims priority to and benefit of U.S. Provisional Patent Application No. 61/912,655, filed Dec. 6, 2013, entitled, "Systems and Methods for Implant," the entire disclosures of which are herein incorporated by reference.

FIELD OF THE DISCLOSURE

Embodiments of the present disclosure are directed generally to systems and methods for delivering a monofilament implant to a body vessel of a patient.

BACKGROUND OF THE DISCLOSURE

PCT publication no. WO2013/179137 discloses various medical implants. Some of these implants comprise an un-deployed and a deployed state. In the un-deployed state, the implant is substantially linear, and in the deployed state the implant assumes a shape directed at providing a medically beneficial function. The implants are typically made of super elastic alloy, such as nitinol. The implants disclosed in the patent documents mentioned above include embolic protection devices for preventing brain stroke and pulmonary embolism, body vessel occlusion devices, stents, and delivery platforms for therapeutic agents (for example, drugs and ionizing radiation).

The implants are typically delivered via a thin needle and a pusher/plunger configured to be slidably received within the lumen of the needle. Initially the implant is disposed in its un-deployed, substantially linear state near the distal end of the needle's lumen, and the pusher is disposed within the lumen proximally to the proximal end of the implant. In operation, the needle is directed by an operator to a suitable implantation site, such as, for example, an artery or a vein. Once the desired needle position is achieved, the pusher is used to push the implant out of the distal end of the needle. As the implant is exteriorized it assumes its functional deployed shape inside the target vessel. Following complete exteriorization of the implant from the needle, the needle and the pusher are withdrawn from the patient's body, and the implantation procedure is complete.

Since the lumen of the delivery needle is typically of very small diameter (e.g., ranging from 0.05 to 0.5 mm), as well as the pusher diameter being equally correspondingly small (e.g., also ranging from 0.05 to 0.5 mm), the pusher may buckle under the push force required for pushing the implant out of the needle.

Since the operator typically uses ultrasound imaging to guide the implantation procedure, the operator typically holds an ultrasound probe in one hand and the delivery system in the other hand. As a result, the operator may need another person in manipulating the delivery system. For example, the operator may need the help of another person in exteriorizing the implant by pushing the pusher. This complicates the delivery procedure.

Moreover, it may be crucial that the implant be sized accordingly with respect to at least one of its dimensions to specific sizes according to the desired functionality. A sizing mistake may prevent the implant from assuming a correct functional shape inside the vessel.

SUMMARY OF THE DISCLOSURE

In some embodiments, a system for delivering an implantable medical device in a living body is provided, with the system comprising an implant having an un-deployed, substantially linear state and a deployed state, a pusher comprising a push wire and a stabilizing tube rigidly connected together at their respective proximal ends, and a needle having a proximal and a distal end and a lumen therebetween for housing said implant in an un-deployed state. The push wire may be configured to be slidably received within the proximal end of the lumen of needle, and the proximal end of the needle may be configured to be slidably received within the stabilizing tube.

In some such embodiments, such a system may also include one or more of the following features and/or functionality (various combinations of which forming additional embodiments, even on their own):

the implant comprises a monofilament;
  the stabilizing tube may be configured to maintain the push wire substantially collinear with the lumen of the needle even if the push wire buckles;
  upon exteriorization from the needle, the implant may be configured in a deployed state;
  the implant includes a diameter between about 0.05 mm to about 1 mm;
  the system of any of claims 1-5, wherein the needle includes an outer diameter of between about 0.2 mm to about 2 mm;
  the lumen of the needle includes a diameter between about 0.1 mm to about 1.9 mm;
  the lumen of the needle includes a diameter between about one to about two times the diameter of the implant; and/or
  the needle comprises a larger diameter echogenic needle and a smaller diameter vessel-penetrating needle.

In some embodiments, a system for delivering an implantable medical device in a living body is provided which comprises an implant having an un-deployed, substantially linear state and a deployed state, a pusher comprising a push wire, a first needle having a proximal and a distal end and a lumen there-between for housing said implant in an un-deployed state, and a second needle having a proximal and a distal end and a lumen there-between for housing said first needle. The second needle may be configured to be received within the lumen of the first needle, and the push wire may be configured to be slidably received within the lumen of the second needle.

In some such embodiments, such a system may also include one or more of the following features and/or functionality (various combinations of which forming additional embodiments, even on their own):

the implant comprises a monofilament;
  the first needle may be configured to be highly visible upon ultra-sound imaging;
  the second needle may be configured to penetrate the wall of a body vessel;
  the second needle may be slidable within the lumen of the first needle;
  the distal tip of the second needle protrudes a predetermined distance distally to the distal end of the first needle, and the predetermined distance may be greater than the thickness of a target vessel wall;

the first needle and the second needle may be rigidly connected;

the first needle includes an outer diameter between about 0.3 mm to about 1 mm;

the second needle includes an outer diameter between about 0.1 mm to about 0.8 mm;

the first needle may be configured with a diameter sufficient to render it highly visible under ultrasound guidance;

in one or more of the needle, the first needle, and the second needle the outer diameter at the distal end may be smaller than the outer diameter at the proximal end;

in one or more of the needle, the first needle, and the second needle the outer diameter may be configured to continuously transition from a smaller distal end to a larger proximal end;

in one or more of the needle, the first needle, and the second needle the outer diameter may be configured to transition from a smaller distal end to a larger proximal end in a stepped configuration;

in one or more of the needle, the first needle, and the second needle may be configured with a rough surface;

in one or more of the needle, the first needle, and the second needle may be configured with ultrasound reflection enhancement means;

the reflection enhancement means comprises at least one of cornerstone reflectors and an echogenic coating;

the echogenic coating comprises at least one microbubble;

the outer diameter of the second needle may be less than about 0.5 mm;

the outer diameter of the second needle may be less than about 0.3 mm;

the inner diameter of the second needle may be less than about 0.4 mm;

the inner diameter of the second needle may be less than about 0.25 mm;

a needle stabilizing tube including a lumen therein;

the lumen of the needle stabilizing tube may be configured to receive the first needle;

the needle stabilizing tube may be rigidly joined to the second needle;

the needle stabilizing tube may be rigidly joined to the second needle at a predetermined point along the length of second needle;

a handle disposed and rigidly connected to the second needle proximate the positions of the needle and the stabilizing tube which may be joined;

the outer diameter of the first needle may be between about 0.2 mm and about 1 mm;

the implant may be arranged in an un-deployed state adjacent the distal end of the lumen of the second needle;

the push wire may be slidably received in the proximal end of the lumen of the second needle;

a pusher stabilizing tube configured to slidably receive the proximal end of the second needle at its distal end;

the second needle may be configured to be slidably received in the proximal end of the lumen of the first needle;

the needle stabilizing tube slidably receives the proximal end of the first needle; and/or in an initial configuration, the distal tip of the second needle may be arranged within the lumen of the first needle.

In some embodiments, a system for delivering an implant in a living body may be provided and comprises implant manipulation means, and a needle. In some such embodiments, such a system may also include one or more of the following features and/or functionality (various combinations of which forming additional embodiments, even on their own):

an implant;

the implant comprises a monofilament;

the implant manipulation means comprises a pusher, a connector, and a stopper;

the pusher comprises a wire;

the connector comprises a tube having a lumen configured to provide a rigid, severable connection between implant and pusher;

the stopper comprises a tube disposed near the distal end of the lumen of needle;

the stopper includes a lumen and wherein the lumen of the stopper may be configured as a truncated cone;

the stopper may be rigidly connected to the needle;

the stopper may be integral with the needle;

a distal end of the connector may be configured to receive a proximal end of the implant;

the connector may be configured to receive at its proximal end the distal end of pusher;

the connector may be configured to rigidly engage both the proximal part of the implant and the distal part of the pusher;

rigid engagement comprises static friction;

the static friction force may be of sufficient strength to pull the implant into the needle by pulling the pusher, without severing the connection made by the connector between the implant and the pusher;

the static friction force may be configured to enable the pusher and the implant to slide through the lumen of the connector when sufficient push-force may be applied to the pusher and the connector may be kept motionless;

the static friction force may be configured via at least one of: the connector being comprised of a heat-shrinkable plastic, and optimizing at least one of the connector's length, initial luminal diameter, and wall thickness;

both the pusher and the connector may be configured to be slidably received within the lumen of the needle;

the implant may be configured to be slidably received in an un-deployed state within the distal end of the lumen of the needle;

the implant may be exteriorized by sliding the pusher within the lumen of the needle until the distal end of the connector may be in contact with the proximal end of the stopper;

the connector may be prevented from further advancing distally in the lumen of the needle;

upon substantial exteriorization of the implant from the needle, the pusher may be configured for continual pushing while the needle may be held in place thereby releasing the implant from the connector;

the connector may be engaged with the implant and/or the pusher via at least one of one or more fasteners, a bayonet configuration, and a positive locking mechanism;

the implant manipulation means comprises a pusher comprising an electrically conducting core and an insulating coating, and the connector comprising an insulator, wherein an area of the conducting cores lacks the insulating coating such that electric current may be applied in the core thereby electrolyzing the conductor in the vicinity of the area;

the system may be configured to recapture a partially exteriorized implant by pulling the manipulation means with respect to the needle;

the implant manipulation means comprises at least one of a push tube, and a disengagement wire;

a wire handle;

the disengagement wire may be configured to be slidably received within a proximal end of the lumen of the push tube;

the implant manipulation means may be configured to be slidably received within a proximal end of the lumen of the needle;

the implant may be configured to be slidably received in an un-deployed state within a distal end of a lumen of the needle;

a distal end of the push tube mechanically engages a proximal end of the implant;

a proximal end of the implant may be inserted in a distal end of a lumen of the push tube, and the connection may be held together by static friction;

the implant may be exteriorized by sliding the implant manipulation means within the lumen of the needle;

the system may be configured to recapture a partially exteriorized implant by pulling the manipulation means with respect to the needle;

the implant may be configured to be disengaged from the implant manipulation means; and/or disengagement comprises pushing the stopper distally until contact with the proximal end of the needle, then pushing disengagement wire distally, thereby exteriorizing the proximal end of the implant from the distal end of the lumen of the push tube;

In some embodiments, a system for delivering an implant in a living body is provided and comprises a driving mechanism, a pusher, and a needle. In some such embodiments, such a system may also include one or more of the following features and/or functionality (various combinations of which forming additional embodiments, even on their own):

an implant;

the pusher comprises a push wire and a rack;

a stabilizing tube;

the rack may be joined to the stabilizing tube on an outside wall thereof;

the rack may be collinear with the stabilizing tube;

the rack assumes the shape of a toothed strip;

the rack may be cylindrically symmetrical;

the driving mechanism comprises a motor having a motor axis and a spur gear rotated by the motor axis;

the motor axis may be substantially perpendicular to the needle;

the rack may be configured to engage with a spur gear via interlocking of teeth of the rack with teeth of the spur gear, and rotation of the spur gear causes the pusher to move relative to the needle;

input means for controlling the rotation of the motor;

the driving mechanism comprises a motor, a worm gear, and optionally a spur gear, where the worm gear comprises helical threads configured to engage the teeth of the rack or the spur gear;

the spur gear may be disposed between the worm gear and the rack, the threads of the worm gear may be configured to engage teeth of the spur gear, and the teeth of the spur gear may be configured to engage teeth of the rack;

the axis of rotation of the worm gear correspond with the motor axis;

the motor axis may be substantially parallel to the needle.

one or more of a controller, a CPU, a computer memory, a man-machine interface, and a power supply;

the rack may be configured to engage with the worm gear via interlocking of the teeth of the rack with the threads of the worm gear or via interlocking of the teeth of the rack with the teeth of a spur gear and interlocking the teeth of the spur gear with the threads of the worm gear, where rotation of the worm gear causes the pusher to move relative to the needle;

the driving mechanism may be rigidly joined to the needle;

the driving mechanism comprises a motor coupled to a first roller and a second roller, wherein the motor causes the first roller to rotate;

the push wire may be disposed between the first and the second roller; and/or the force of friction between the first roller and the push wire causes the push wire to advance or retract as a result of roller rotation by the motor.

In some embodiments, a method of delivering an implant in a living body may be provided and comprises providing a system according to any system embodiment supported by the present disclosure, determining the diameter of a target vessel at an implantation site, selecting an appropriate sized implant for the target vessel based on the determined diameter of the target vessel, penetrating the skin adjacent the target vessel via a tip of the needle, advancing the tip of the needle towards the target vessel, penetrating the target vessel using the tip of needle, advancing the pusher toward the distal end of the needle, and withdrawing the needle and the pusher out of the target vessel.

In some such embodiments, such a method may also include one or more of the following features and/or functionality (various combinations of which forming additional embodiments, even on their own):

upon the implant comprising a stem, the pusher may be configured such that the distance between the distal tip of the pusher and the distal end of the needle may be approximately equal to the length of the stem, resulting in the implant assuming a correct position within the target vessel;

the method may be performed under imaging guidance comprising at least one of ultrasound, high resolution ultrasound, x-ray fluoroscopy, CT, and MRI;

advancing comprises placing a tip of the needle a predetermined distance from the vessel puncture site;

the implant assumes a predetermined orientation after exteriorization;

upon the implant being an embolic protection device, a tip of the needle may be placed about 1 mm into the lumen of the target vessel;

the needle assumes an approximately perpendicular orientation with respect to a plane tangent to the arterial wall at the puncture site;

the implant may be preloaded in the system;

selection of the implant comprises selecting the maximal diameter of the deployed state of the implant may be between about 0.5 to about 1 mm less than the diameter of the vessel;

selecting of the appropriately sized implant comprises under-sizing the implant along at least one dimension of the implant relative to the diameter of the target vessel; and/or oversizing the implant along another dimension of the implant relative to the diameter of the target vessel.

In some embodiments, a system for delivering an implant in a living body is provided and comprises an implant, a needle, a pusher, a connector configured to reversibly attach the implant and the pusher, the implant may be exteriorized from the needle by pushing the pusher, the implant may be interiorized in the needle by pulling the pusher, and the implant may be disconnected from the connector by pushing the pusher.

In some embodiments, a removable implant system is provided and comprises a pusher, a removable implant comprising a monofilament and a pull-wire, wherein the pull wire is affixed to or integral with an end of the monofilament and configured to extend outside the body of a patient a predetermined distance when the implant is implanted to enable the implant to be pulled out of the vessel, and wherein the implant includes a un-deployed and a deployed stat, and a needle. The pusher comprises a hollow tube having a lumen.

In some embodiments, a removable implant configured for placement within a target vessel of a patient is provided, where the implant comprises a monofilament and a pull-wire. The pull wire is affixed to or integral with an end of the monofilament and configured to extend outside the body of a patient a predetermined distance when the implant is implanted to enable the implant to be pulled out of the vessel, and wherein the implant includes an un-deployed and a deployed state.

In some embodiments, the implant may include one or more of the following:
- an anchor;
- the pull-wire is affixed at one end to the filament via at least one of welding, brazing, gluing, or by means of a mechanical connector;
- the monofilament and/or pull-wire are affixed to the anchor via at least one of welding, brazing, gluing, or crimping;
- at least a portion of the monofilament in the deployed state includes a substantially straight stem configured to traverse a wall of a target vessel, where the stem may be configured to secure the implant in place;
- in the deployed state, the implant further comprises a functional portion configured in the shape of a helix, where the helix traces a shape corresponding to a shell of a body of revolution which may include a sphere, an oval, or an ellipsoid, and upon implantation, the axis of the helix may be configured approximately perpendicular to the direction of the vessel; additionally, the length of the helix may be configured to be greater than the diameter of the target vessel, and the diameter of the helix is less than the diameter of the target vessel;
- an anchor configured to reside near the proximal end of the stem (see above feature), where the anchor includes an un-deployed state configured to fit within the lumen of a delivery needle, and a deployed state configured to adhere to surrounding tissue, and the anchor may comprise one or more barb, one or more protrusion, or one or more micro-barb;
- the pull-wire includes a circular cross section with a diameter of between about 0.03 mm and 1.0 mm;
- the needle comprises metal or plastic, and an outer diameter of the needle ranges between about 0.2 mm to about 2 mm, and/or an inner diameter of the needle ranges between 0.1 mm to 1.9 mm;
- the pull-wire is configured such that at least a portion thereof is slidably fits within lumen of the pusher;
- the pusher is configured to slidably fit within the lumen of the needle;
- the monofilament includes an anchor, and the pusher is configured to push either on the proximal end of the monofilament or on a proximal end of the anchor; and/or
- the pusher is initially arranged in a proximal end of the lumen of the needle, proximally to the monofilament and the anchor, with at least a portion of the pull-wire arranged within the lumen of the pusher.

In some embodiments, a method of implanting the monofilament implant according to any of the disclosed implant embodiments using any of the system embodiments disclosed herein is provided and may comprise at least one of the following steps, and in some embodiments, several of the following steps, and in some embodiments, substantially all of the following steps: assessing the size of a target vessel via at least one of ultrasound, fluoroscopy, CT, or MM, upon the vessel being an artery or a vein, a systolic or minimal diameter at the implantation site is measured and recorded, selecting an appropriately sized implant, where at least a portion of the implant is configured as a helix when deployed, the helix diameter being between 0.1 mm and 1.0 mm compared to the minimal vessel diameter at the implantation site, wherein the selected implant is preloaded within one or another of the disclosed system embodiments, puncturing the skin of the patient, advancing a tip of the needle towards the target vessel, puncturing the wall of the target vessel using the tip of the needle, placing the tip in the lumen of the target vessel approximately in the middle of the lumen of the vessel, where the needle may assume an approximately perpendicular orientation with respect to a plane tangent to the vessel wall at the puncture site, advancing the pusher towards the distal end of the needle, resulting in the implant being exteriorized from the needle, where the exteriorized portion of the implant is configured to resume the deployed shape. The method may further include one or more of further advancing the pusher until its proximal end is aligned with the proximal end of the needle, verifying proper positioning and/or shape of the deployed monofilament within the target vessel lumen, and withdrawing the needle and the pusher.

The method embodiments may further include one or more of the following steps and/or functionality (for the method, system and/or implant):
- the implant further comprises an anchor, and the anchor slides out of the tip of the needle as the needle is being pulled, and the pull-wire slides out of the pusher lumen;
- the implant further comprises a stem portion, and upon complete withdrawal of the needle and the pusher, a functional portion of the monofilament is arranged within the lumen of the target vessel, the stem traverses the vessel wall, the anchor is arranged external to the vessel wall and under the skin, and/or the pull-wire traverses the patient's skin;
- inspecting the implantation area for proper positioning and/or deployment of the implant using a suitable imaging modality using at least one of ultrasound, x-ray, fluoroscopy, MRI or CT;
- upon a permanent implantation, and upon proper positioning and/or deployment of the implant, clipping the pull-wire at the level of skin, and lifting the skin thereafter to arrange the remainder of the pull-wire subcutaneously;
- upon the implant intended for removal due to temporary nature of use, or for removal due to safety concerns, pulling the pull wire to cause the monofilament to deform for exteriorization from the target vessel and from the patient's body;

the system further including a motor configured to advance the pusher, for effecting advancement of the pusher via a gear and/or a rack.

Advantages of Some Embodiments of the Disclosure

Some embodiments according to the present disclosure have several important advantages over prior art.

Some embodiments may be more reliable because the deleterious effects of pusher buckling may be diminished.

Some embodiments may be safer to use because they enable removal of the implant from the patient's body following complete (satisfactory or unsatisfactory) exteriorization from the delivery system.

Some embodiments may be safer because they enable the implant to be interiorized into the delivery system following partial (or even near-complete) unsatisfactory exteriorization.

Some embodiments may be safer because they allow for better needle visualization by ultrasound.

Some embodiments may be safer because they eliminate the tradeoff between needle visibility under ultrasound and a small vessel wall puncture size.

Some embodiments enable a single-operator ultrasound-guided procedure because they are automatic.

Some embodiments may be easier to use because they are automatic.

BRIEF DESCRIPTION OF THE DRAWINGS

The invention may be better understood with reference to the accompanying drawings and subsequently provided detailed description:

FIGS. 4A-E depict an implant system according to some embodiments of the present disclosure. Under certain conditions the system allows for interiorization of the implant back into the needle lumen.

DETAILED DESCRIPTION OF SOME OF THE EMBODIMENTS

Figure 1A:
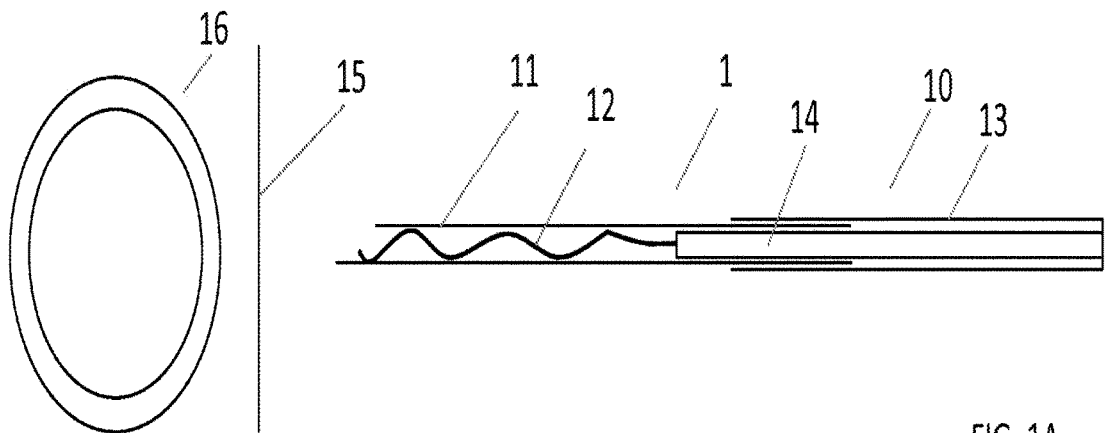
FIGS. 1A-E depict an implant system and its corresponding method of use according to some embodiments of the present disclosure. The system comprises a pusher that configured to diminish the effect of buckling.

Reference is now made to FIGS. 1A-E, which depict an implant system and method for implant delivery according to some embodiments of the present disclosure. System 1 may comprise a pusher 10, an implant 12, and a needle 11. Pusher 10 may comprise a push wire 14 and a stabilizing tube 13.

The push wire and the stabilizing tube may be rigidly connected at their proximal ends by a suitable method such as, for example, welding, gluing, or screwing. Push wire 14 is configured to be slidably received within the proximal end of the lumen of needle 11. Stabilizing tube 13 is configured to slidably receive the proximal end of needle 11.

Stabilizing tube 13 diminishes the deleterious effect of buckling of wire 14 as it is being pushed into the lumen of needle II. This is because stabilizing tube 13 may be made sufficiently stiff as to not buckle under the push force required to slide implant 12 within the lumen of needle 11, and push wire 14, even if it buckles, is kept by the internal walls of stabilizing tube 13 substantially collinear with the lumen of needle 11. Push wire 13 is thus able to transmit push force from its proximal to its distal end even if it buckles.

Push wire 14 may be made from metal or plastic. Suitable metals include, for example, stainless steel and nitinol. Stabilizing tube 13 may also be made from metal or a plastic. Suitable metals include, for example, stainless steel and nitinol.

Implant 12 may be made from a super elastic alloy, such as nitinol. The implant may be of monofilament construction (as depicted in FIG. 1A), but may also may be of a different construction (for example, a multi-filament construction or a cut-tube construction). The implant assumes an un-deployed, substantially linear state (as in FIG. 1A) or a deployed, functional state (as in FIG. 1E). The implant is constrained to its un-deployed substantially linear state by the needle, in whose distal lumen end it initially resides. Upon exteriorization from the needle (FIGS. 1C-1E), the implant retains its deployed, functional state by virtue of its super-elasticity.

Whenever implant 12 is a monofilament implant, the wire from which it is made may have a circular cross-section. The diameter may range from about 0.05 mm to about 1 mm.

Implant 12 may be an embolic protection device for stroke prevention, an embolic protection device for pulmonary embolism prevention, a vessel occlusion device such as a left atrial appendage occluder, a therapeutic agent delivery platform a stent, or any other medical implant that fits in its un-deployed state into the lumen of a thin needle. Implant 12 may be any implant that can be twisted into its functional shape from a monofilament. Implant 12 may be, but is not limited to, any of the implants described in U.S. Provisional Patent Applications Nos. 61/653,676, 61/693,979, 61/746, 423, 61/754,264, as well as PCT publication nos. WO2013/179137, WO2014/102767 and WO2014/111911 (the entire disclosures of which all herein incorporated by reference).

In some embodiments, the functional, deployed state of implant 12 may comprise a substantially straight stem 17, configured to traverse the wall of a target vessel 16 and anchor the implant in place, and a functional portion 18, configured to perform a beneficial medical function (FIG.

1E). If, for example, implant 12 is an embolic protection device then functional portion 18 resembles the shape of a helix. The helix is implanted with its axis perpendicular to the blood flow in the vessel, and (sufficiently large) emboli originating upstream of the implant may be prevented by the helix coils from flowing past the implant. The helix of monofilament embolic protection devices according to some embodiments may be configured to trace the shape of a cone or an hour glass. Such devices may have a stem intended for traversing a vessel wall. The stem may be perpendicular to the helix axis.

Needle 11 may be made from metal or plastic. Suitable metals include, for example, stainless steel and nitinol. The outer diameter of the needle may range from about 0.2 mm to 2 mm. The inner diameter of the needle may range from 0.1 mm to 1.9 mm.

Whenever implant 12 is a monofilament implant, the inner diameter of needle 11 may be between one and two times the diameter of the wire from which implant 12 is made. We have found in laboratory experiments that this minimizes the push force required to insert and/or advance implant 12 in the lumen of needle 11.

In operation, the operator first assesses the size of target vessel 16. Typically, the assessment is made by, for example, ultrasound, fluoroscopy, CT, or MRI. If, for example, the vessel is an artery or a vein, the systolic (minimal) diameter of the vessel at the implantation site is measured and recorded. The operator then chooses an appropriately sized implant 12 (preloaded in system 1). Whenever implant 12 is a monofilament implant, the operator chooses the implant size according to the following rule: the maximal diameter of the deployed state of the implant should be about 0.5 to 1.5 mm less than the systolic diameter of the vessel. In some embodiments under-sizing may be required in order to allow for the implant to properly exteriorize and assume its functional, deployed shape.

Figure 1B:
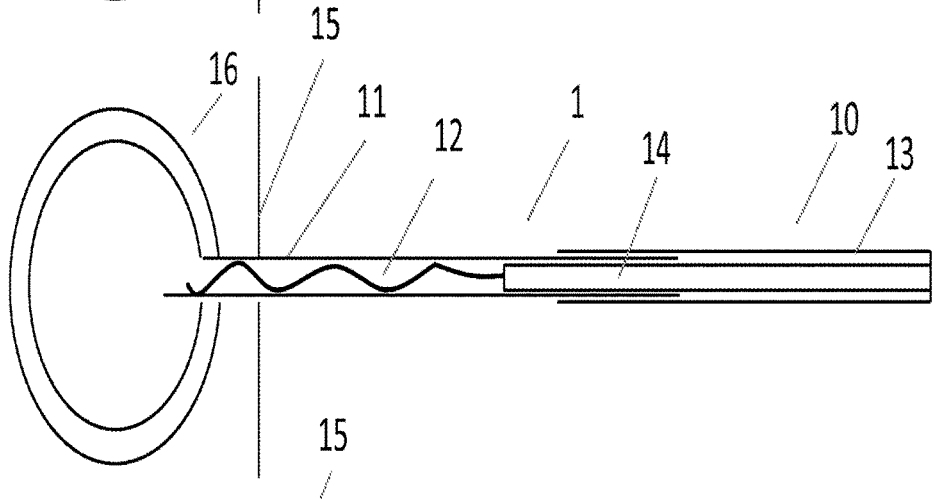
Figure 1C:
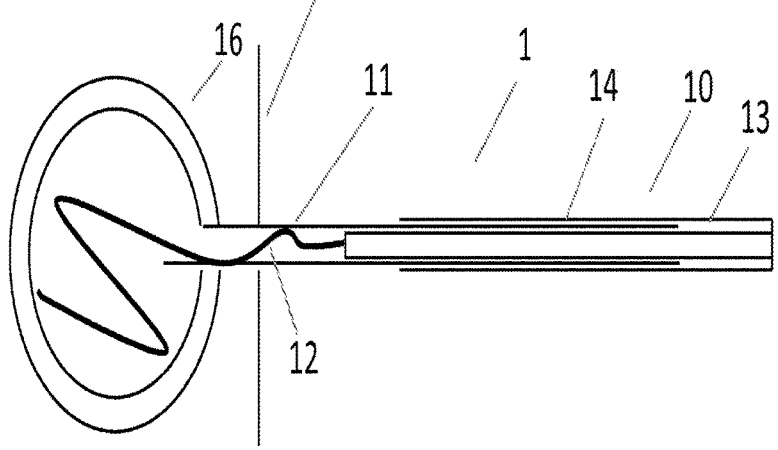
Figure 1D:
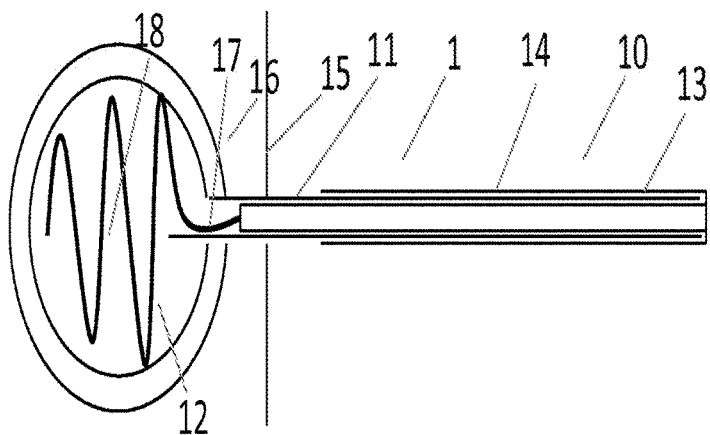

Next, the operator punctures skin 15, advances the tip of needle 11 towards the target vessel 16, and punctures target vessel 16 using the tip of needle 11 (FIG. 1B). All of these steps may be performed under imaging guidance. Possible imaging modalities include ultrasound, high resolution ultrasound, x-ray fluoroscopy, CT, and MRI. The tip is placed a predetermined distance from the vessel puncture site, and the needle assumes a predetermined orientation. For example, if implant 12 is an embolic protection device, then the tip of needle 11 is placed about 1 mm into the lumen of vessel 16. The needle assumes a perpendicular orientation with respect to a plane tangent to the arterial wall at the puncture site. Whenever the operator determines that either the tip is placed improperly or the needle orientation is improper, system 1 may be retracted and the present step of the procedure may be attempted again.

Once proper needle position has been achieved, the operator holds needle 11 steady and advances pusher 10 towards the distal end of the needle (FIG. 1 C). This causes implant 12 to be exteriorized from the needle. The exteriorized portion of the implant attempts to assume its functional deployed shape.

The operator continues to push pusher 10 until its proximal end touches the proximal end of needle 11. Whenever implant 12 comprises a stem 17 pusher 10 may be configured such that at the position described in FIG. 1D the distance between the distal tip of the pusher and the end of the needle is approximately equal to the length of the stem. In some embodiments, this enables the implant 12 to assume the correct orientation within the vessel.

Figure 1E:
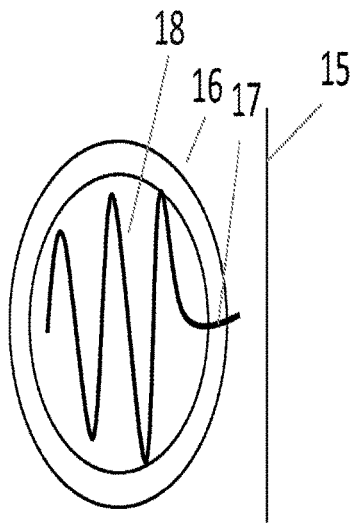

Next, the operator verifies using an appropriate imaging modality that the implant is properly positioned and withdraws the needle and the pusher out of the patient's body (FIG. 1E). The implantation procedure is complete.

Figure 2A:
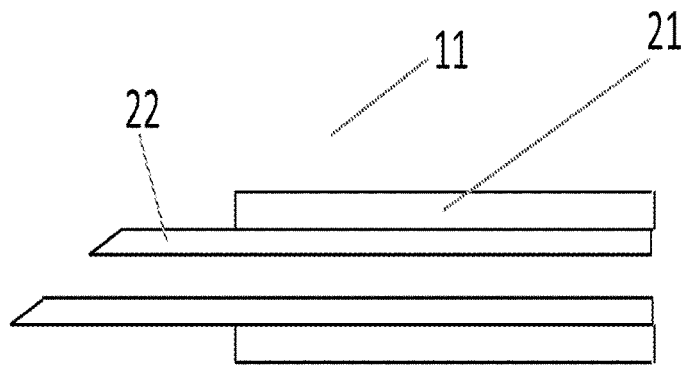
FIG. 2A-C depict various needle designs according to some embodiments of the present disclosure. These designs render the needle more visible under ultrasound imaging and less traumatic to the target vessel.
Figure 2B:
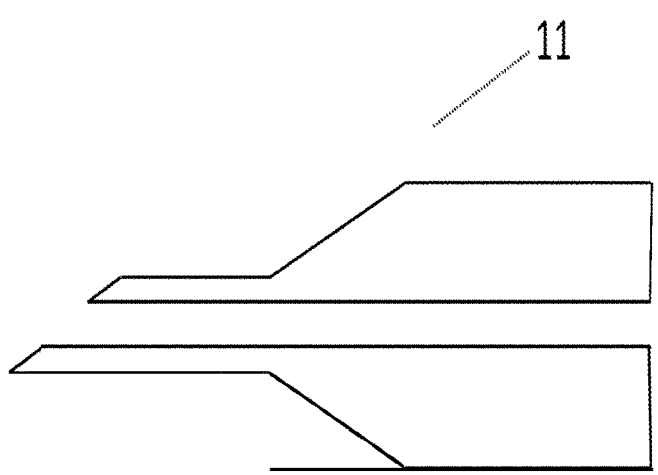
Figure 2C:
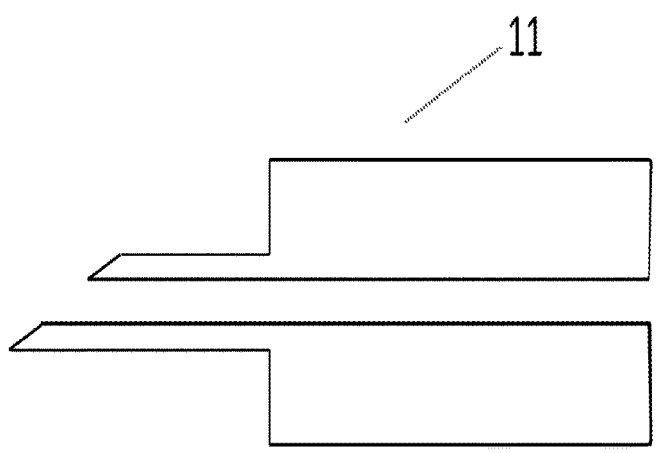

Reference is now made to FIGS. 2A-C, which depict various designs according to some embodiments of needle 11 of system 1. Needle 11 need not be of uniform outer diameter. Furthermore, needle 11 need not be of monoblock construction. For example, needle 11 may comprise a first larger diameter needle 21 and a second smaller diameter vessel-puncturing needle 22 (FIG. 2A). The second needle 22 is housed within the lumen of the first needle 21. The distal tip of second needle 22 protrudes a predetermined distance distally to the distal end of first needle 21. This distance is typically somewhat larger than the thickness of the target vessel wall. The two needles may be connected using a suitable means such as, for example, gluing, or welding. First needle 21 may have an outer diameter ranging from about 0.3 mm to about 1 mm, and second needle 22 may have an outer diameter ranging from about 0.1 mm to about 0.8 mm. First needle 21 may be made out of metal, such as, for example, stainless steel or nitinol. The same goes for second needle 22.

In operation, the operator may use ultrasound guidance to advance the needle of FIG. 2A towards the target vessel. As the first needle 21 is clearly visible (whereas the tip of second needle 22 need not be ultrasound visible), the operator punctures the vessel wall by advancing the tip of the first needle adjacent to the vessel wall. The second needle 22, whose sharp distal end protrudes beyond the distal end of first needle 21, thus penetrates the vessel wall.

The embodiment of needle 11 depicted in FIG. 2A has the following advantages: (I) safety: the second needle may have a very small outer diameter, thereby causing minimal reducing trauma to the vessel wall. For example, the outer diameter of second needle 22 may be less than 0.5 mm, or even less than 0.3 mm. (2) The first needle may have a diameter sufficient to render it highly visible under ultrasound guidance. For example, the diameter of the first needle 21 may be greater than 0.5 mm, or even greater than 0.8 mm; (3) The first needle 21 may have an outer diameter sufficiently large as to make needle 11 sufficiently stiff to penetrate towards structures deep in the patient's body. Thus, the embodiment of needle 11 according to FIG. 2A eliminates the inherent tradeoff existing in uniform-outer-diameter needles: ultrasound visibility and stiffness on the one hand against a small outer diameter facilitating minimally-traumatic punctures.

Reference is now made to FIGS. 2B and 2C, which depict some embodiments of needle 11 according to the present disclosure. In both cases the outer diameter of the distal end of the needle is smaller than the outer diameter of the proximal end of the needle. In FIG. 2B the transition from the smaller to the larger outer diameter is continuous, whereas in FIG. 2C it is discontinuous (that is, a step or a multi-step transition). The operation of systems I comprising the needles 11 according to FIGS. 2B and 2C is similar to the operation of systems based on the needle of FIG. 2A, and will therefore be omitted. The advantages of the needles II according to FIGS. 2B and 2C are also essentially the same as for the needle of FIG. 2A. The needles of FIG. 2B-C may be made out of metal, such as, for example, stainless steel or nitinol. The needles may be given their shapes by, for example, machining.

The needles of FIGS. 2A-C may be made echogenic by roughening their surfaces, providing them with ultrasound reflection enhancement means, such as cornerstone reflectors, or coating them with echogenic coatings such as a micro-bubble-containing polymer coating.

Reference is now made to FIGS. 3A-F, which depict an implant system and a method for implant delivery according to some embodiments of the present disclosure. System 3 may comprise an implant 12, a first echogenic needle 35, a second needle 36, and a pusher 31.

Implant 12, which may (but does not have to be) a monofilament implant, is substantially similar to the implant of system 1, and therefore its detailed description will be omitted here.

Second needle 36 may be made, for example, from plastic or metal. Suitable metals include, for example, stainless steel and nitinol. The outer diameter of second needle may be less than about 0.5 mm, or even less than about 0.3 mm. The inner diameter of second needle may be less than about 0.4 mm, or even less than 0.25 mm. Optionally, a needle stabilizing tube 38 may be configured to receive first needle 35 in its lumen. Tube 38 may be rigidly joined to second needle 36 at a predetermined point along the length of second needle 36. Optionally, a handle 37 may be disposed and rigidly connected to second needle 36 at the vicinity of the point where needle 36 and tube 38 are joined.

First needle 35 may be made, for example, from plastic or metal. Suitable metals include, for example, stainless steel and nitinol. The outer diameter of first needle 35 may range from about 0.2 mm to about 1 mm.

Pusher 31 may have a similar construction to pusher 13 of system 1: pusher 13 may comprise a push wire 34 and optionally a pusher stabilizing tube 33, which may be joined at their proximal ends. Optionally, pusher 31 may comprise a pusher handle 32.

Initially (FIG. 3A), implant 12 situated in the un-deployed state near the distal end of the lumen of second needle 36. Push wire 34 is slidably received in the proximal end of the lumen of second needle 36. Stabilizing pusher tube 33 slidably receives at its distal end the proximal end of second needle 36. Second needle 36 is slidably received in the proximal end of the lumen of first needle 35. Needle stabilizing tube 38 slidably receives the proximal end of first needle 35. Initially, the distal tip of second needle 36 is within the lumen of first needle 35.

In operation, the operator first assesses the size of target vessel 16. Typically, the assessment is made by, for example, ultrasound, fluoroscopy, CT, or MRI. If, for example, whenever the vessel is an artery or a vein, the systolic (minimal) diameter of the vessel at the implantation site is measured and recorded. The operator then chooses an appropriately sized implant 12 (preloaded in system 3). Whenever implant 12 is a monofilament implant the operator may choose the size according to the following rule: the maximal diameter of the deployed state of the implant should be about 0.5 to 1 mm less than the systolic diameter of the vessel. Undersizing is required in order to allow for the implant to properly exteriorize and assume its functional, deployed shape.

Figure 3A:
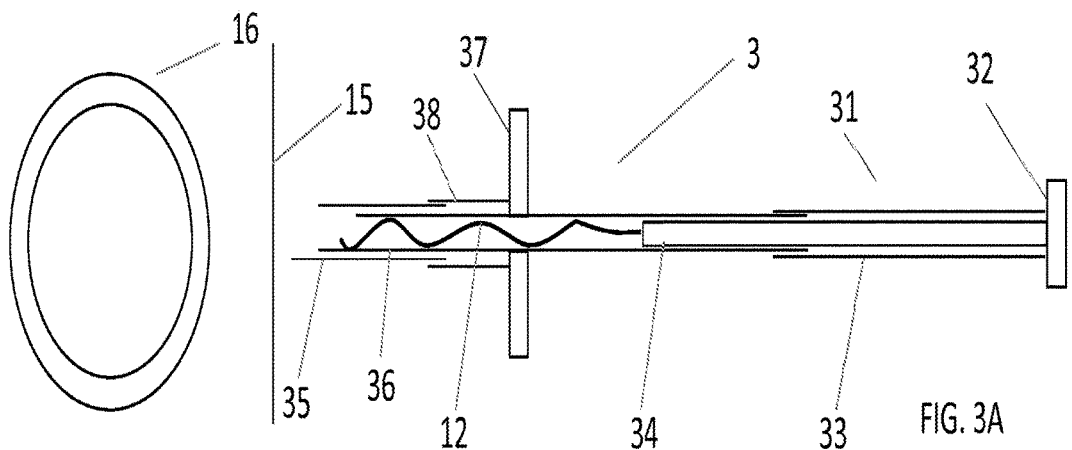
FIGS. 3A-F depict an implant system and its corresponding method of use according to some embodiments of the present disclosure. The system comprises a first introducer needle and a second, vessel-puncturing needle that is slidable within the introducer needle lumen.
Figure 3B:
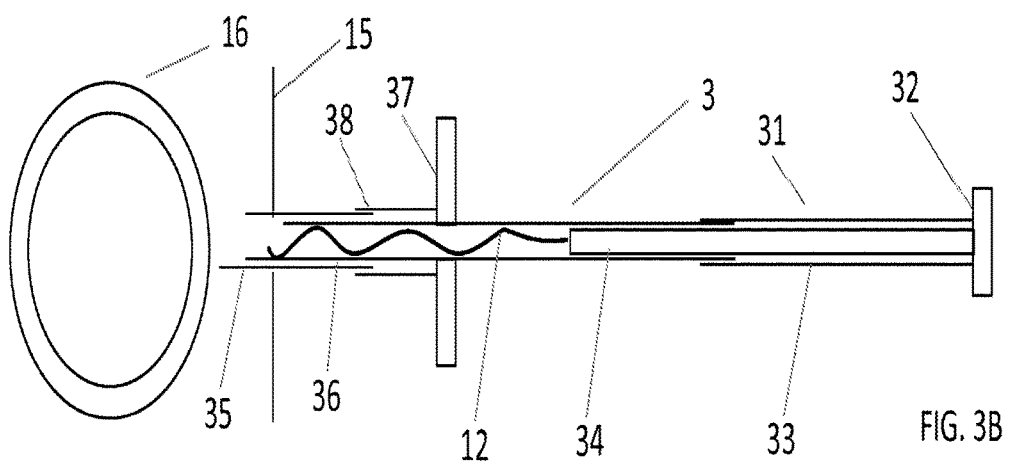

Next, the operator punctures skin 15 using the tip of first needle 35 and advances the tip of needle 35 towards the target vessel 16 (FIG. 3B). All of these steps may be performed under imaging guidance. Possible imaging modalities include ultrasound, high resolution ultrasound, x-ray fluoroscopy, CT, and MRI. The tip of first needle 35 is placed a predetermined distance from the vessel puncture site, and the needle assumes a predetermined orientation. For example, if implant 12 is an embolic protection device, then the tip of needle 35 is placed about 1 mm outside of the wall of vessel 16. The needle assumes a perpendicular orientation with respect to a plane tangent to the arterial wall at the puncture site. Whenever the operator determines that either the tip is placed improperly or the needle orientation is improper, system 3 may be retracted and the present step of the procedure may be attempted again.

Figure 3C:
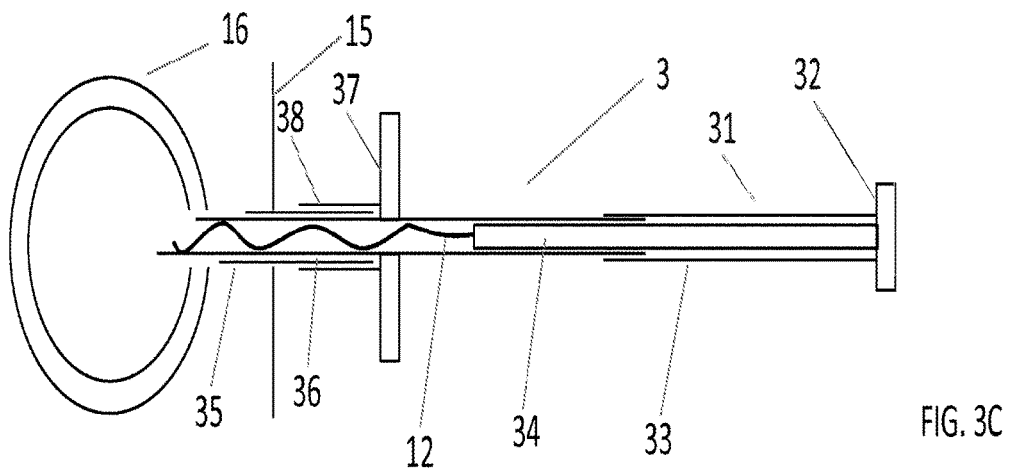

Once proper needle position has been achieved, the operator holds needle 35 steady and advances handle 37 towards the distal end of needle 35 (FIG. 3C). This causes second needle 36 to exteriorize from the lumen of first needle 35 and puncture the vessel wall. The pushing of handle 37 ceases when the proximal end of first needle 35 reaches handle 37 (and, optionally, the proximal end of stabilizing tube 38, which prevents the bucking of needle 36).

Figure 3D:
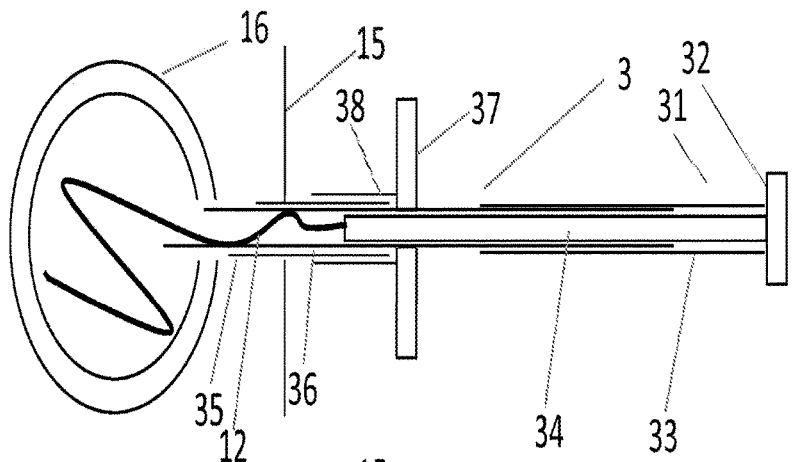
Figure 3E:
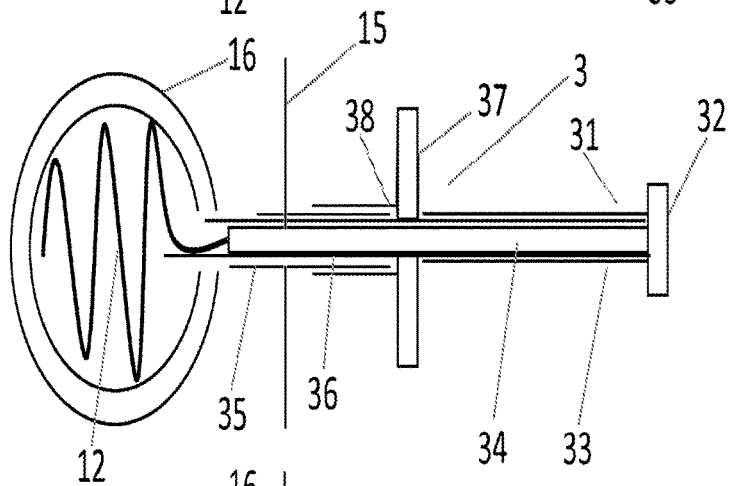

Next, the operator holds needles 35 and 36 steady and advances pusher 31 towards the distal end of needle 36 (FIG. 3D). This causes implant 12 to be exteriorized from the needle. The exteriorized portion of the needle attempts to assume its functional shape.

The operator continues to push pusher 31 until its proximal end touches the proximal end of second needle 36. Whenever implant 12 comprises a stem 17 pusher 31 may be configured such that at the position depicted in FIG. 3E the distance between the distal tip of the push wire 34 and the end of needle 36 is approximately equal to the length of the stem. This enables the implant 12 to assume the correct orientation within the vessel.

Figure 3F:
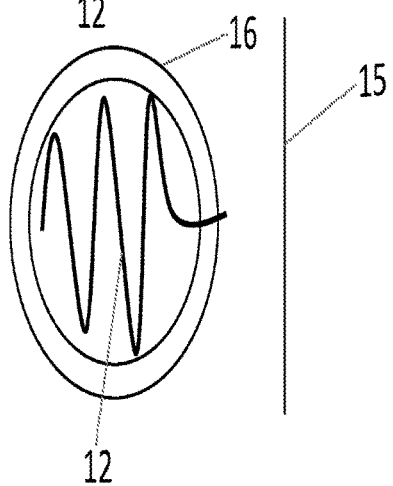

Next, the operator verifies using an appropriate imaging modality that the implant is properly positioned and withdraws the needles and the pusher out of the patient's body (FIG. 3F). The implantation procedure is complete.

An embodiment of system 3 lacking implant 12 and in which second needle 36 is configured as a biopsy needle is possible.

System 3 has the following important advantages: (1) ease of use: initially, the tip of the second needle is inside the lumen of the first needle. Therefore confusion between the tips of the two needles upon ultrasound visualization is eliminated; (2) safety: the second needle may have a very small outer diameter, thereby making the puncture in the vessel wall correspondingly small and non-traumatic; (3) the needle-in-needle configuration provides desired stiffness during system insertion.

Reference is now made to FIGS. 4A-E, which depict an implant system according to some embodiments of the present disclosure. System 4 may comprise an implant 12, implant manipulation means 40, and a needle 43.

Implant 12, which may (but does not have to) be a monofilament implant, is substantially similar to the implant of systems 1 and 3. Needle 43 may be substantially similar to needle 11 of system 1. Therefore a detailed description of implant 12 and needle 43 is omitted.

Implant manipulation means 40 may comprise a pusher 41, a connector 42, and a stopper 44.

Pusher 41 may be substantially similar to pusher 10 or to push wire 14 of system 1.

Connector 42 may be configured as a tube having a lumen, whose function is to provide a rigid yet severable connection between implant 12 and pusher 41. The connector may be made, for example, from metal, plastic, or heat-shrinkable plastic.

Stopper 44 may be a tube disposed near the distal end of the lumen of needle 43. The lumen of stopper 44 may be of uniform diameter, or it might have a varying diameter. The lumen of stopper 44 may have the shape of a cone with the apex cut off. Stopper 44 may be made from metal. The stopper may be rigidly connected to the needle by, for example, welding, soldering, or brazing. Stopper 44 may be integral with needle 43. Whenever the stopper is integral with the needle it may be made by, for example, machining the needle.

Connector 42 may be configured to receive at its distal end the proximal end of implant 12. Connector 42 may also be configured to receive at its proximal end the distal end of pusher 41. The connector may be configured to rigidly engage both the proximal part of implant 12 and the distal part of pusher 41 by static friction. The static friction force may be configured sufficiently large such that pulling the implant into the needle (by pulling the pusher) is possible without severing the connection made by connector 42 between implant 12 and pusher 41. The static friction force may also be simultaneously configured to be sufficiently small as to enable the pusher and implant to slide through the lumen of the connector when sufficient push-force is applied to the pusher and the connector is kept motionless.

Providing appropriate static friction force may be achieved by one or more of making the connector from heat-shrinkable plastic and optimizing the connector's length, initial luminal diameter, and wall thickness.

Both pusher 41 and engagement mechanism 42 may be configured to be slidably received within the lumen of needle 43. Implant 12 is configured to be slidably received in its un-deployed state within the distal end of the lumen of needle 43.

Implant 12 is exteriorized by sliding pusher 41 within the lumen of needle 43 until the distal end of connector 42 is in contact with the proximal end of stopper 44 (FIG. 4B). The connector is thus prevented from further advancing distally in the lumen of needle 43. When the implant is in the position depicted in FIG. 4B, it is possible to exteriorize the implant completely by continuing to push the pusher. The continued pushing causes the pusher to slide within the lumen of connector 42, thereby overcoming the friction force between connector 42 and implant 12, thus pushing the proximal part of implant 12 out of the lumen of the connector (FIG. 4O). Needle 43 and manipulation means 40 may then be retracted, leaving behind implant 12 in the deployed state (FIG. 4E).

It is also possible interiorize a partially exteriorized implant 12 by pulling the pusher with respect to needle 43. The pull force is transmitted to implant 12 via the static friction force between connector 42 and both of implant 12 and pusher 41 (FIG. 4C).

The operation of system 4 is substantially similar to the operation of system 1, except for the following step. Following near-complete exteriorization (FIG. 4B) of the implant from the needle, the operator verifies using a suitable imaging modality that the implant is properly deployed in the target vessel. If this is the case then the operator continues to push the pusher while holding the needle in place, thereby releasing the implant from the connector (FIG. 4O) and withdraws from the patient's body all non-implantable elements of the system (FIG. 4E). Otherwise, the operator holds needle 43 steady and pulls pusher 41 back, thereby interiorizing implant 12 into the needle lumen. The operator may then attempt the procedure once more.

It is possible for connector 42 to engage implant 12 and/or pusher 41 by any mechanical means known in the art. Suitable mechanical means may include, screwing, a bayonet, and a positive locking mechanism. It is possible to make the pusher from an electricity conducting core and an insulating coating. The connector may also be made from an insulator. A nick may be made in the insulating coating of the pusher. Electric current may be run in the core, thereby electrolyzing the conductor in the vicinity of the nick. This mechanism, similar to the detachment mechanism of embolization coils, may be used to detach the implant and the connector from the pusher.

In some embodiments, stopper 44 may be optional.

Reference is now made to FIGS. 5A-D, which depict an implant system according to some embodiments of the present disclosure. System 5 may comprise an implant 12, an implant manipulation means 51, a needle 56, and a stopper 54.

Implant 12, which may (but does not have to) be a monofilament implant, may be substantially similar to the implant of systems 1 and 3. Needle 56 may be substantially similar to needle 11 of system 1. Therefore a detailed description of implant 12 and needle 56 is omitted.

Implant manipulation means 51 may comprise a push tube 52, a disengagement wire 53, and, optionally, wire handle 55. Disengagement wire is configured to be slidably received thin (the proximal end of) the lumen of push tube 52.

Implant manipulation means 51 is configured to be slidably received within the proximal end of the lumen of needle 56. Implant 12 is configured to be slidably received in its un-deployed state within the distal end of the lumen of needle 56.

The distal end of push tube 52 mechanically engages the proximal end of implant 12: the proximal end of implant 12 is inserted in the distal end of the lumen of push tube 52. The connection is held together by static friction.

Figures 5A, 5B, 5C, 5D:
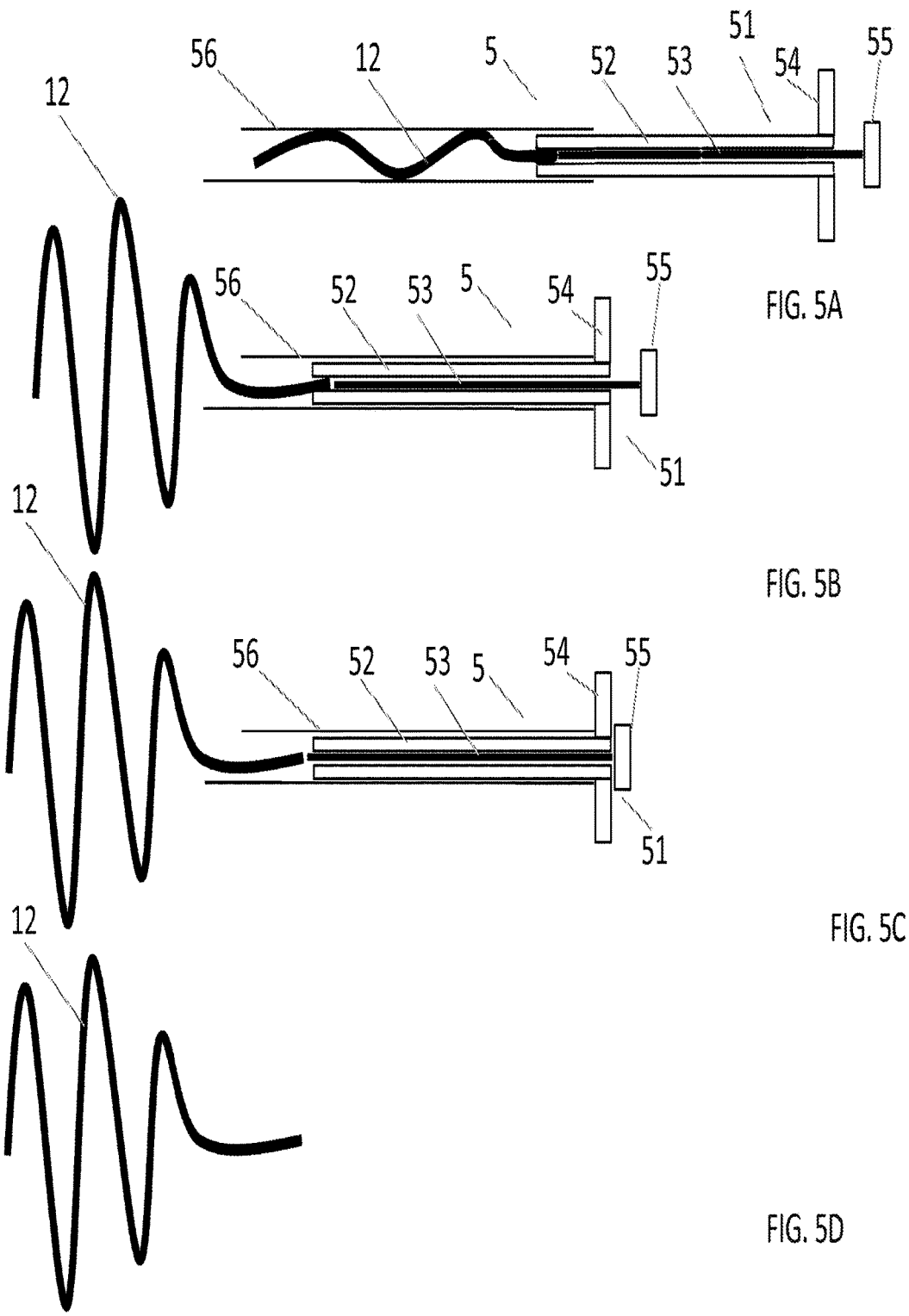
FIGS. 5A-D depict an implant system according to some embodiments of the present disclosure. The system features mechanical engagement and disengagement of the implant and the pusher.

Implant 12 is exteriorized by sliding implant manipulation means 51 within the lumen of needle 56 (FIG. 5B). It is also possible interiorize a partially exteriorized implant 12 by pulling the manipulation means with respect to needle 56.

Implant 12 may be disengaged from implant manipulation means 51 in the following way: The stopper 54 is pushed distally until it contacts the proximal end of needle 56. This causes the disengagement wire to be pushed distally, thereby exteriorizing the proximal end of implant 12 from the distal end of the lumen of push tube 52.

The operation of system 5 is substantially similar to the operation of system 1, except for the following step. Following near-complete exteriorization of the implant from the needle, wherein the proximal end of implant 12 is engaged with the distal end of push tube 52 and the stopper 54 is in contact with the proximal end of needle 56 (FIG. SB), the operator verifies using a suitable imaging modality that the implant is properly deployed in the target vessel. If this is the case then the operator pushes the disengagement wire handle distally and thereby disengages the implant from the push tube (FIG. 5C). Then the operator withdraws from the patient's body all non-implantable elements of the system. Otherwise, the operator holds needle 56 steady and pulls pusher 51 back, thereby interiorizing implant 12 into the needle lumen. The operator may then attempt the procedure once more.

The systems according to the embodiment presented in FIGS. 4A-E and 5A-D have the advantage of improved safety: an improperly exteriorized implant may be withdrawn back into the needle, thereby obviating the need to extract a mal-deployed implant using minimally invasive or even surgical means.

Figure 6A:
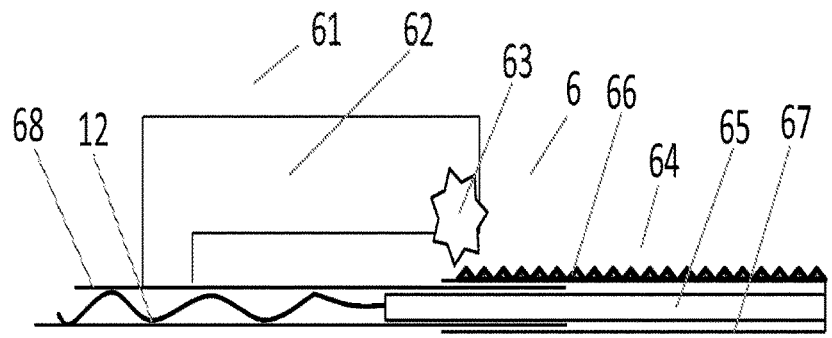
FIGS. 6A-C depict an automatic delivery system comprising a motor according to some embodiments of the present disclosure. The motor axis is approximately perpendicular to the needle.
Figure 6B:
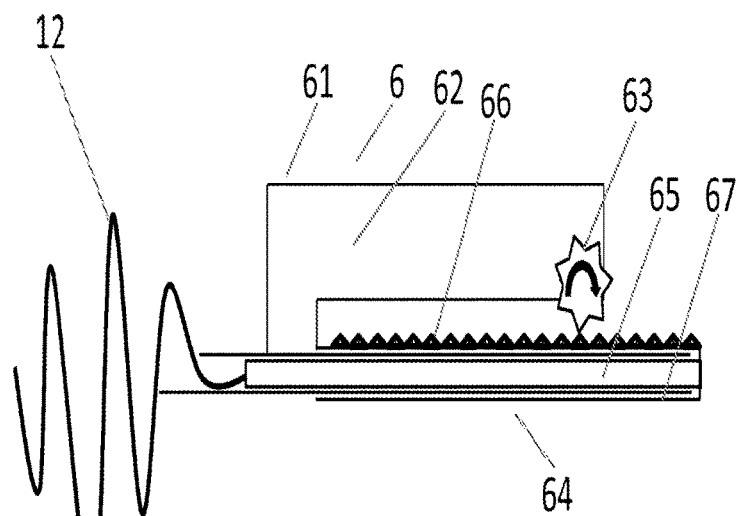
Figure 6C:
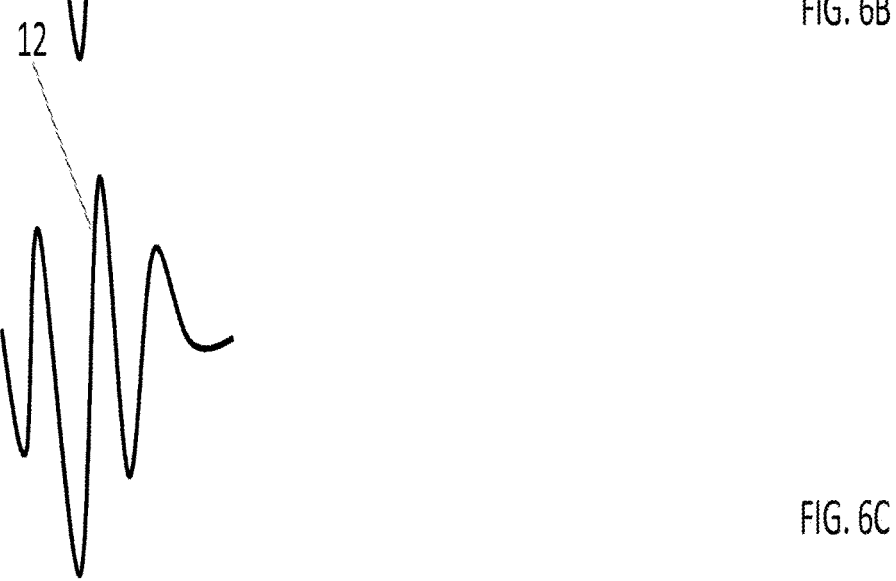

Reference is now made to FIGS. 6A-C, which depict an automatic implant system according to some embodiments of the present disclosure. Automatic implant system 6 may comprise an implant 12, a driving mechanism 61, a pusher 64, and a needle 68. Implant 12, which may (but does not have to) be a monofilament implant, may be substantially similar to the implant of systems 1 and 3. Needle 68 may be substantially similar to needle 11 of system 1. Therefore a detailed description of implant 12 and needle 68 is omitted.

Pusher 64 may comprise push wire 65, stabilizing tube 67, and rack 66. Push wire 65 is substantially similar to push wire 14 of system 1, and stabilizing tube 67 is substantially similar to stabilizing tube 13 of system 1. The push wire and the stabilizing tube may be rigidly joined at their proximal end using a suitable joining technique (for example, gluing, welding, or soldering). Rack 66 is joined to stabilizing tube 65 on its outside wall. Rack 66 may be collinear with stabilizing tube 65 as in FIG. 6A. The rack may assume the shape of a toothed strip. It may also be cylindrically symmetrical. The rack may be integral with the stabilizing tube, or it may be separate from it.

Driving mechanism 61 may comprise a motor 62 and a spur gear 63, which is rotated by the motor axis. The motor axis is substantially perpendicular to the needle. Driving mechanism 61 may be rigidly joined to needle 68. Driving mechanism 61 may also comprise one or more of a controller, a CPU, a computer memory, a man-machine interface, and a power supply (all not shown).

Initially, implant 12 is loaded in its un-deployed shape in the distal lumen of needle 68. Push wire 65 of pusher 64 is slidably received in the proximal end of the lumen of needle 68. The distal end of stabilizing tube 67 slidably receives the proximal end of needle 68. Rack 66 is configured to engage with spur gear 63 via interlocking of the teeth of the rack with the teeth of the spur wheel. Thus, rotation of the spur wheel causes pusher 64 to move relative to needle 68.

The operation of system 6 is substantially similar to the operation of system 1 except for the following difference: instead of manually pushing the pusher in order to exteriorize implant 12 from needle 68, the operator causes pusher 66 to exteriorize the implant by providing instructions (via, for example, buttons comprised in the man machine interface) to driving mechanism 61.

System 6 has the following important advantages: (1) it enables single handed operation by a single operator, and; (2) In reduces inter-operator variability because of automation.

Figure 7A:
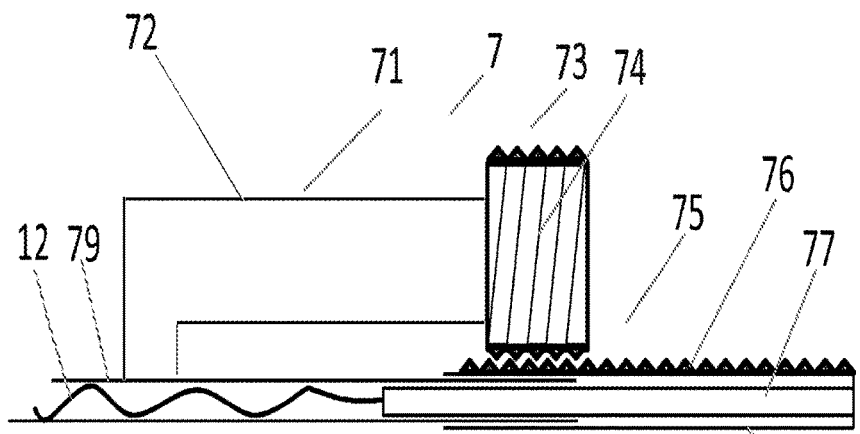
FIGS. 7A-C depict an automatic delivery system comprising a motor according to some embodiments of the present disclosure. The motor axis is approximately parallel to the needle.
Figure 7B:
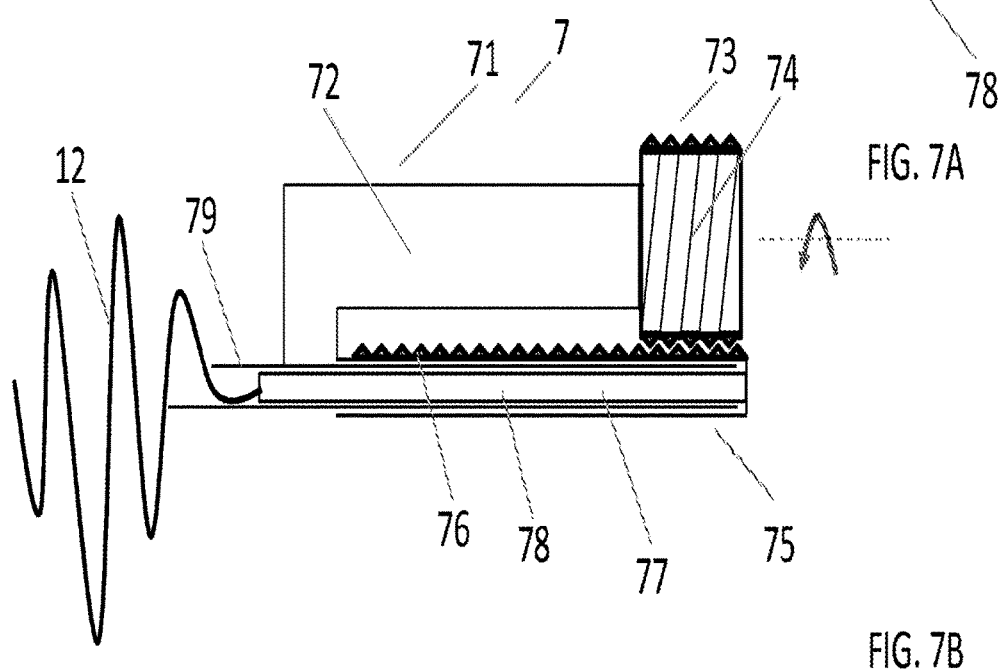
Figure 7C:
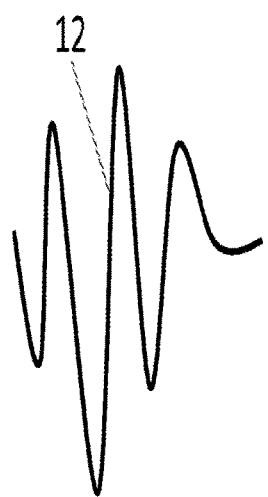

Reference is now made to FIGS. 7A-C, which depict an automatic implant system according to some embodiments of the present disclosure. Automatic implant system 7 may comprise an implant 12, a driving mechanism 71, a pusher 75, and a needle 79.

Implant 12, which may (but does not have to) be a monofilament implant, may be substantially similar to the implant of systems 1 and 3. Needle 79 may be substantially similar to needle 11 of system 1. Therefore the detailed description of implant 12 and needle 79 is omitted.

Pusher 75 is substantially similar to pusher 64 of system 6. Push wire 77, stabilizing tube 78, and rack 76 may be substantially similar to their counterpal is 65, 67, and 66 in pusher 64. Therefore a detailed description of pusher 75 is omitted.

Driving mechanism 71 may comprise a motor 72 and a worm 74 having helical threads configured to engage the teeth of rack 76. The worm's rotation axis is identical with the motor axis. The motor axis is substantially parallel to the needle. Driving mechanism 71 is joined rigidly to needle 79. Driving mechanism 71 may also comprise one or more of a controller, a CPU, a computer memory, a man-machine interface, and a power supply (all not shown).

Initially, implant 12 is loaded in its un-deployed shape in the distal lumen of needle 79. Push wire 77 of pusher 75 is slidably received in the proximal end of the lumen of needle 79. The distal end of stabilizing tube 78 slidably receives the proximal end of needle 79. Rack 76 is configured to engage with worm 73 via interlocking of the teeth of the rack with the threads of the worm. Thus, rotation of the worm causes pusher 75 to move relative to needle 79.

The operation of system 7 is substantially similar to the operation of system 6.

System 7 has the following important advantages: (1) It enables single-handed operation by a single operator; (2) In reduces inter-operator variability because of automation, and; (3) the parallel orientation of the motor axis and the needle makes for good ergonomic design.

Figure 8A:
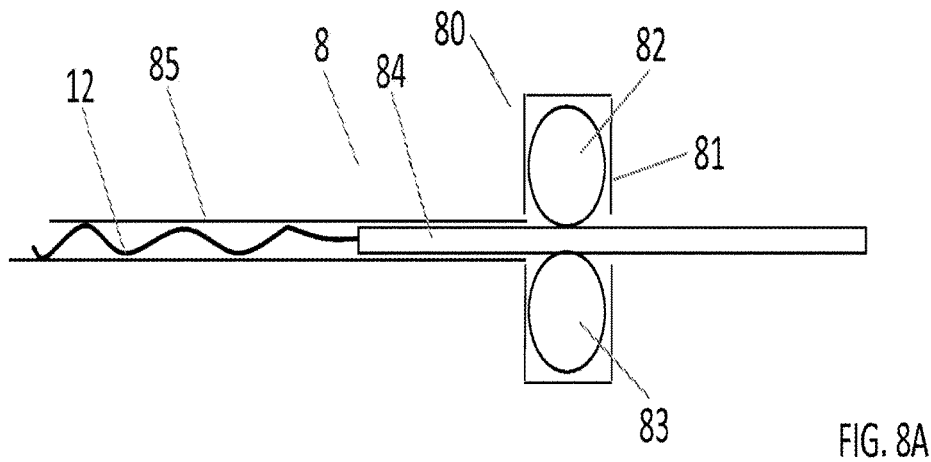
FIGS. 8A-C depict an automatic delivery system in which power is transmitted from a motor to a push wire via rollers.
Figure 8B:
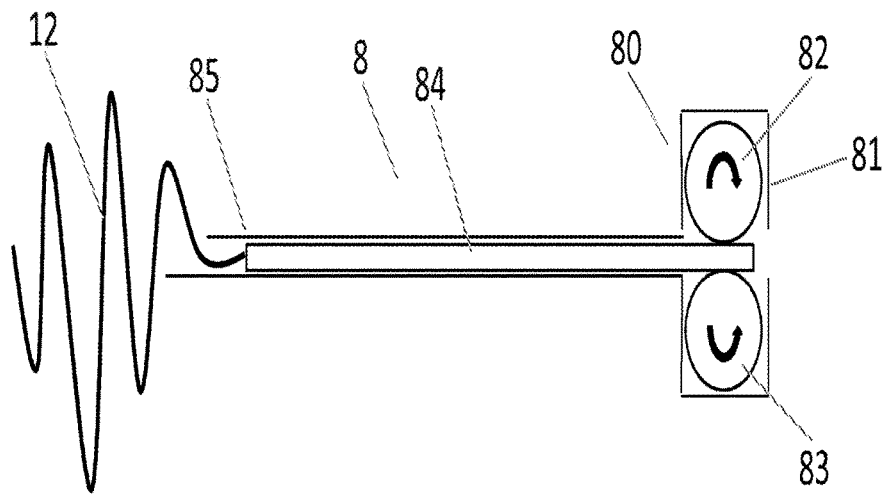
Figure 8C:
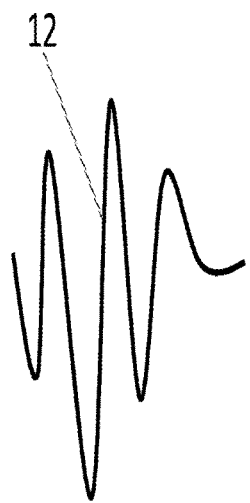

Reference is now made to FIGS. 8A-C, which depict an automatic implant system according to some embodiments of the present disclosure. Automatic implant system 8 may comprise a monofilament implant 12, a driving mechanism 80, a push wire 84, and a needle 85.

Implant 12, which may (but does not have to) be a monofilament implant, may be substantially similar to the implant of systems 1 and 3. Needle 85 may be substantially similar to needle 11 of system 1. Therefore the detailed description of implant 12 and needle 85 is omitted.

Push wire 84 is substantially similar to push wire 14 of system 1. Therefore a detailed description of push wire 14 is omitted.

Driving mechanism 80 may comprise a motor 81 coupled to a first roller 82 and a second roller 83. Motor 81 causes roller 81 to rotate. Push wire 84 is disposed between the first and the second roller. The force of friction between the first roller and the push wire causes the push wire to advance or retract as a result of roller rotation by the motor.

Driving mechanism 80 is joined rigidly to needle 85. Driving mechanism 80 may comprise one or more of a controller, a CPU, a computer memory, a man-machine interface, and a power supply (all not shown).

Initially, implant 12 is loaded in its un-deployed shape in the distal lumen of needle 85. Push wire 84 is slidably received in the proximal end of the lumen of needle 85. Push wire 84 may initially have a substantially linear configuration, or it may have a more spatially compact form. For example, push wire 84 may initially be rolled on a spool (not shown) in order to save space in system 8.

The operation of system 8 is substantially similar to the operation of system 6.

System 8 has the following advantages: (1) it enables single-handed operation by a single operator; (2) In reduces inter-operator variability because of automation, and; (3) It is conductive towards an ergonomic, compact design because the push wire may be initially disposed on a spool or in a coil.

Reference is now made to FIGS. 9A-H, which depict a removable implant system and method for implant delivery and potential removal according to some embodiments of the present disclosure.

System 9 may comprise a pusher 90, a removable implant 91, and a needle 92. Pusher 90 may be a hollow tube having a lumen 97 therethrough. Pusher 90 may be made from, for example, a metal such as stainless steel, or from plastic.

Removable implant 91 may comprise a monofilament 93, an anchor 94 (optional), and a pull-wire 98. Monofilament 93 and pull-wire 98 may be one and the same, or alternatively, monofilament 93 and pull-wire 98 may be separate components. The proximal end of monofilament 93 may be joined to the distal end of pull-wire 98 by any suitable method known in the art, such as welding, brazing, gluing, or by means of a mechanical connector. Monofilament 93 and pull-wire 98 may each be joined to anchor 94 by, for example, welding, brazing, gluing, or crimping.

Monofilament 93 may be made from a super-elastic alloy, such as nitinol, and may be made from a wire having a circular cross-section, with a diameter between about 0.05 mm and about 1.0 mm (for example). Monofilament 93 may assume an un-deployed, substantially linear state (as in FIG. 9A) or a deployed, functional state (as in FIG. 9E). The monofilament is constrained to its un-deployed, substantially linear state by the needle, where the monofilament initially resides in the distal lumen end thereof. Upon exteriorization from the needle (FIGS. C, D), the monofilament retains its deployed, functional state by virtue of its super-elasticity.

Implant 91 may have the same uses as implant 12 and may have any functional, deployed shape realizable by twisting monofilament 93. Monofilament 93 may have, but is not limited to have, a functional shape similar to that of any of the implants described in the PCT publications incorporated by reference herein (see paragraph [0046]).

In some embodiments, the functional, deployed state of implant 91 may comprise a substantially straight stem 95, configured to traverse the wall of a target vessel 16 and secure the implant in place, and a functional portion 96, configured to perform a beneficial medical function. If, for example, implant 91 is an embolic protection device, then functional portion 96 resembles the shape of a helix. The helix may trace a shape similar to a shell of a body of revolution, such as, for example, a sphere, an oval, or an ellipsoid. The helix is implanted with its axis approximately perpendicular to the direction of the vessel (which, in arteries, for example, is the same as the direction of the blood flow). Thus, sufficiently large emboli originating upstream of the implant may be prevented by the helix coils from flowing past the implant.

The length of the helix may be greater than the diameter of the vessel, thereby ensuring contact between the distal end of the helix and the vessel wall as the helix is compressed along the direction of its axis. Growth of cells from the vessel wall (neointimal formation) on the distal end of the helix may further secure implant 91 in place. The diameter of the helix may be less than the diameter of the vessel, thereby ensuring proper deployment.

Anchor 94 may reside near the proximal end of stem 95. Anchor 94 may have, for example, an un-deployed state configured to fit within the lumen of needle 92, and a deployed state configured to adhere to surrounding tissue. Anchor 94 may be made from nitinol. The anchor may comprise, for example, one or more barb, one or more protrusion, or one or more micro-barb.

Pull-wire 98 may have a circular cross section. The diameter of pull-wire 98 may be between 0.03 mm and 1.0 mm. Pull-wire 98 may be made, for example, of metal, a super-elastic alloy (nitinol), a polymer, or a biodegradable polymer.

Needle 92 may be made from metal or plastic, with suitable metals including, for example, stainless steel and nitinol. The outer diameter of the needle may range from about 0.2 mm to about 2 mm. The inner diameter of the needle may range from 0.1 mm to 1.9 mm.

Pull-wire 98 may be configured such that at least a portion of it slidably fits within lumen 97 of pusher 90. Pusher 90 may be configured to slidably fit within the lumen of needle 92. Pusher 90 may also be configured to push either on the proximal end of monofilament 93 or on the proximal end of anchor 94. Pusher 90 is initially arranged in the proximal end of the lumen of needle 92, proximally to monofilament 93 and anchor 94, with at least a portion of pull-wire 98 within pusher lumen 97.

In operation, the operator first assesses the size of target vessel 16. Typically, the assessment is made by, for example, ultrasound, fluoroscopy, CT, or MM. If, for example, the vessel is an artery or a vein, the systolic (minimal) diameter at the implantation site is measured and recorded. The operator then chooses an appropriately sized implant 91 (preloaded in system 9). If, for example, the functional portion of monofilament 93 is a helix, then the helix diameter may be chosen undersized between 0.1 mm and 1.0 mm compared to the minimal vessel diameter at the implantation site.

Figure 9A:
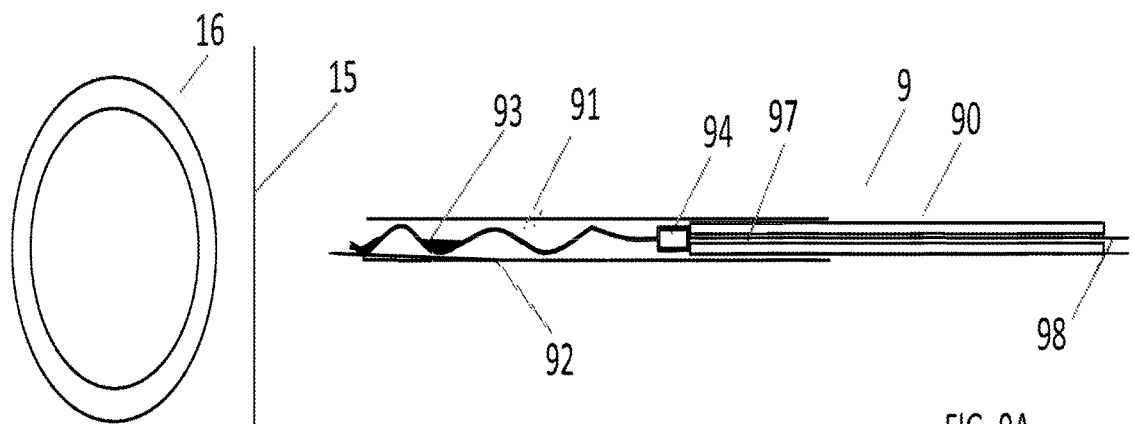
FIGS. 9A-H depict a removable implant system and its corresponding method of use according to some embodiments of the present disclosure.
Figure 9B:
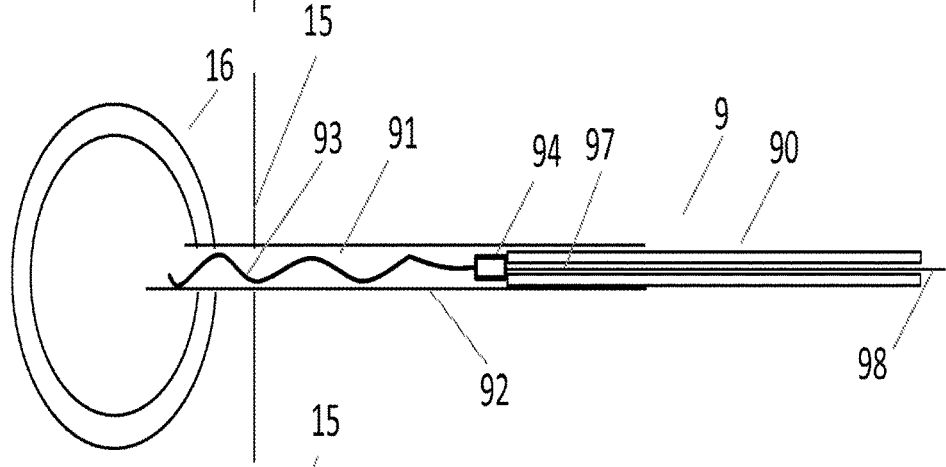

Next, the operator punctures skin 15, advances the tip of needle 92 towards the target vessel 16, and punctures vessel 16 using the tip of needle 92 (FIG. 9B). All of these steps may be performed under imaging guidance. Possible imaging modalities include ultrasound, high resolution ultrasound, z-ray fluoroscopy, CT, and MM. The tip is placed in the lumen of the vessel, approximately in the middle of the lumen of the vessel. The needle may assume an approximately perpendicular orientation with respect to a plane tangent to the vessel wall at the puncture site.

Figure 9C:
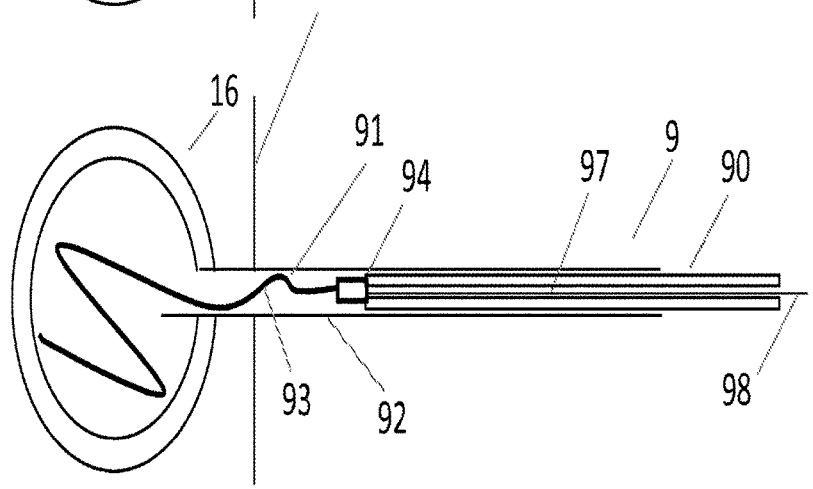
Figure 9D:
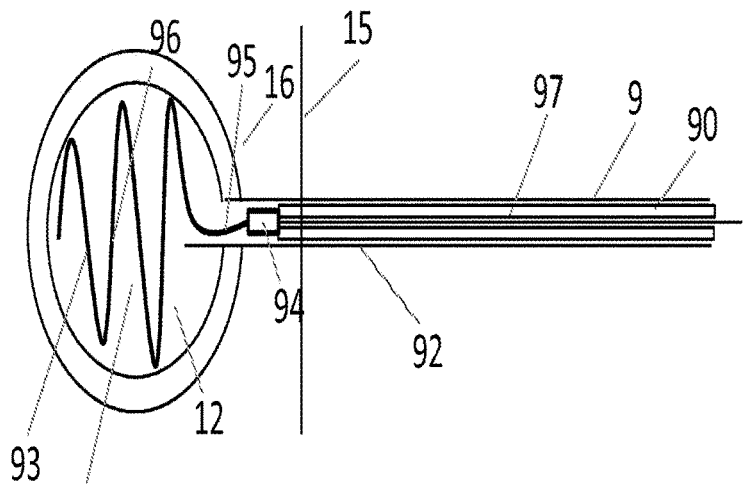

Once proper needle position in the vessel lumen has been achieved, the operator advance pusher 90 towards the distal end of needle 92 while holding the needle steady (FIG. 9C). This causes implant 91 to be exteriorized from the needle. The exteriorized portion of the implant attempts to resume its functional deployed shape.

The operator continues to push pusher 90 until its proximal end is aligned with the proximal end of the needle. Whenever implant 91 comprises a stem 95 and an anchor 94 pusher 90 may be configured such that at the position described in FIG. 9D the distance between the distal end of the pusher and the tip of the needle is approximately equal to the length of the stem. In some embodiments, this enables monofilament 93 to assume the correct orientation within the vessel.

Figure 9E:
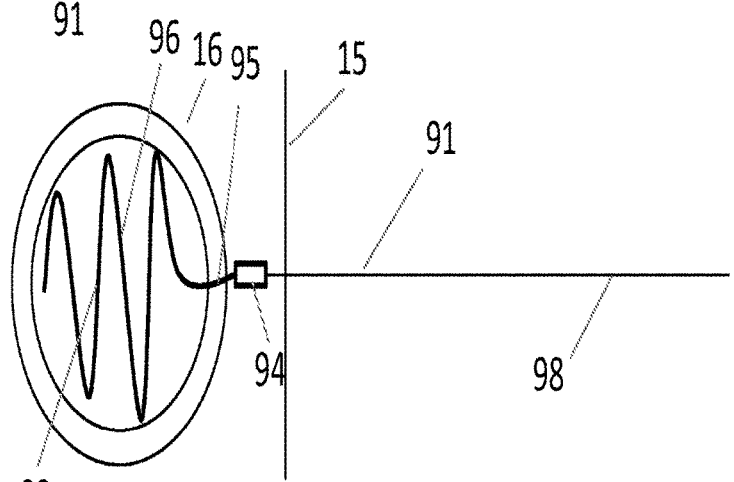

Next, the operator verifies using a proper imaging modality that the monofilament has correctly assumed its functional shape within the vessel lumen. The operator then withdraws the needle and the pusher. The anchor slides out of the tip of the needle as the needle is being pulled, and the pull-wire 98 slides out of pusher lumen 97. The situation depicted in FIG. 9E is achieved upon complete withdrawal of the needle and the pusher: functional portion 96 of monofilament 93 is within the lumen of vessel 16, stem 95 traverses the vessel wall, anchor 94 is external to the vessel wall and under skin 15, and pull-wire 98 traverses the patient's skin.

Figure 9F:
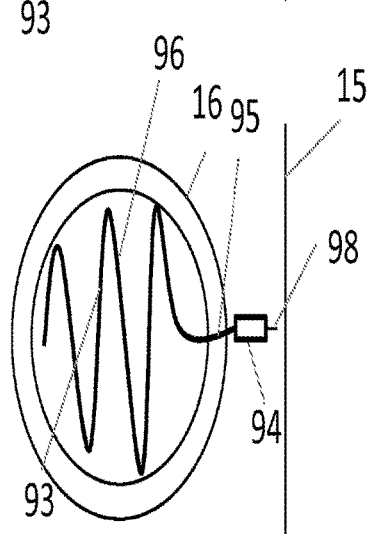

Whenever implant 91 is intended for permanent use, the operator inspects the implantation site using a suitable imaging modality, such as ultrasound, x-ray, fluoroscopy, MRI or CT, anywhere from, for example, minutes to months after the implantation. If the result is satisfactory, the operator clips pull-wire 98 at the level of skin 15 and lifts the skin, thereby placing the entire remainder of the pull-wire subcutaneously. The situation depicted in FIG. 9F is achieved.

Figure 9G:
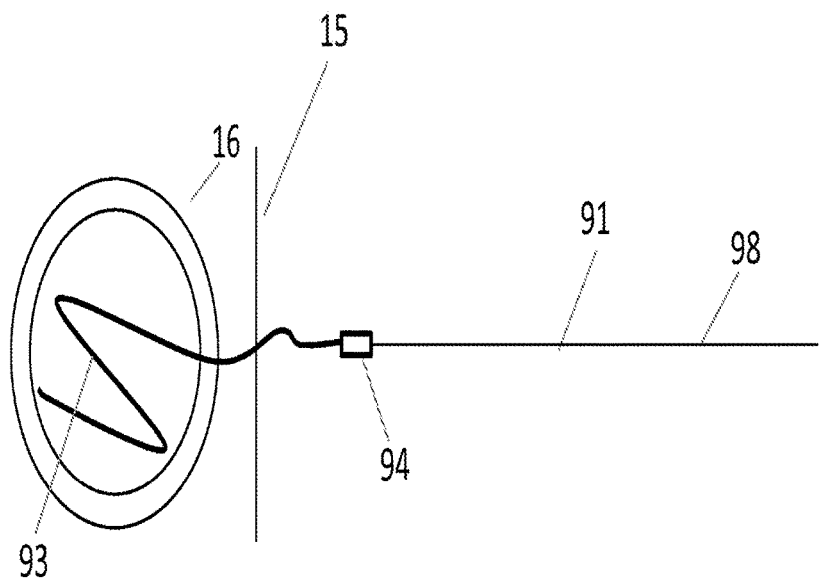
Figure 9H:
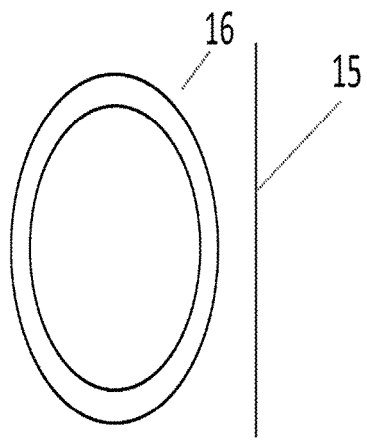

Whenever implant 91 is intended for removal due to the temporary nature of its use, or whenever implant 91 is intended for permanent use but has to be removed due to safety reasons, the operator pulls the pull wire, thereby causing monofilament 93 to deform as in FIG. 9G and be exteriorized from vessel 16 and from the patient's body (FIG. 9H). Monofilament 93 may exit the vessel wall through the breach in which the stem originally resides.

Note that an automatic system having a hollow pusher may be used to deliver implant 91. Operation is similar to that described above for system 9 (except that a motor is used to advance the pusher via a gear and a rack), and therefore detailed description is omitted.

Any and all combinations of the embodiments described herein may be possible. For example automatic systems in which the implant may be retrieved back into the needle are possible.

Example embodiments have been described herein. As may be noted elsewhere, these embodiments have been described for illustrative purposes only and are not limiting. Other embodiments are possible and are covered by the disclosure, which will be apparent from the teachings contained herein. Thus, the breadth and scope of the disclosure should not be limited by any of the above-described embodiments but should be defined only in accordance with features and claims supported by the present disclosure and their equivalents. Moreover, embodiments of the subject disclosure may include formulations, methods, systems and devices which may further include any and all elements/features from any other disclosed formulations, methods, systems, and devices, including the manufacture and use thereof. In other words, features from one and/or another disclosed embodiment may be interchangeable with features from other disclosed embodiments, which, in turn, correspond to yet other embodiments. One or more features/elements of disclosed embodiments may be removed and still result in patentable subject matter (and thus, resulting in yet more embodiments of the subject disclosure). Furthermore, some embodiments of the present disclosure may be distinguishable from the prior art by specifically lacking one and/or another feature, functionality, ingredient or structure which is included in the prior art (i.e., claims directed to such embodiments may include "negative limitations").

Any and all references, articles, publications, patents, patent publications, and patent applications cited herein are incorporated by reference in their entireties for all purposes. However, mention of any reference, article, publication, patent, patent publication, and patent application cited herein is not, and should not be taken as, an acknowledgment or any form of suggestion that they constitute valid prior art or form part of the common general knowledge in any country in the world.

The invention claimed is:

1. A system for delivering an implant in a living body, comprising:
    a pusher, a needle, and a removable implant comprising: a monofilament and a pull-wire,
    wherein:
        the pull-wire is affixed to or integral with an end of the monofilament,
        the pull-wire is configured to extend outside the body of a patient a predetermined distance when the implant is implanted to enable the implant to be pulled out of the vessel, and
        the implant includes a un-deployed and a deployed state,
    and wherein the pusher:
        comprises a hollow tube having a lumen,
        is configured to releasably push on a proximal end of the monofilament, and
        is initially arranged in a proximal end of the lumen of the needle, proximally to the monofilament.

2. The system of 1, wherein at least a portion of the monofilament in the deployed state includes a substantially straight stem configured to traverse a wall of a target vessel.

3. The system of 2, wherein the stem is configured to aid in securing the implant in place.

4. The system of claim 2, wherein implant further comprises at least one of an anchor and a connector, and wherein the anchor is configured to reside near the proximal end of the stem.

5. The system of claim 1, wherein in the deployed state, the implant further comprising a functional portion configured in the shape of a helix, wherein the helix traces a shape corresponding to a shell of a body of revolution.

6. The system of claim 5, wherein the body of revolution comprises a sphere, an oval, or an ellipsoid, or the length of the helix is configured to be greater than the diameter of the target vessel.

7. The system of claim 5, wherein the diameter of the helix is less than the diameter of the target vessel.

8. The system of claim 1, wherein implant further comprises at least one of an anchor and a connector.

9. The system of claim 8, wherein the anchor comprises one or more barb, one or more protrusion, or one or more micro-barb.

10. The system of claim 8, wherein the anchor includes an un-deployed state configured to fit within the lumen of a delivery needle, and a deployed state configured to adhere to surrounding tissue.

11. The system of claim 1, wherein the pull-wire includes a circular cross section with a diameter of between about 0.03 mm and 1.0 mm.

12. The system of claim 1, wherein the needle comprises metal or plastic, and wherein an outer diameter of the needle ranges between about 0.2 mm to about 2 mm, and/or an inner diameter of the needle ranges between 0.1 mm to 1.9 mm.

13. The system of claim 1, wherein the pull-wire is configured such that at least a portion thereof is slidably fits within the lumen of the pusher.

14. The system of claim 1, wherein the pusher is configured to slidably fit within the lumen of the needle.

15. The system of claim 1, further comprising a driving mechanism.

16. The system of claim 1, wherein at least a portion of the pull-wire arranged within the lumen of the pusher.

17. A system for delivering an implant in a living body, comprising:
    a pusher, a needle, and a removable implant including a pull-wire,
    wherein:
        the pull-wire is affixed to or integral with an end of the implant,
        the pull-wire is configured to extend outside the body of a patient a predetermined distance when the implant is implanted to enable the implant to be pulled out of the vessel, and
        the implant includes a un-deployed and a deployed state,
    and wherein the pusher:
    comprises a hollow tube having a lumen,
    is configured to releasably push on a proximal end of the implant, and
    is initially arranged in a proximal end of the lumen of the needle, proximally to the implant.

18. The system of claim 17, further comprising a driving mechanism.

19. The system of claim 17, wherein at least a portion of the pull-wire arranged within the lumen of the pusher.

* * * * *